(12) United States Patent
Shelley et al.

(10) Patent No.: US 7,514,268 B2
(45) Date of Patent: *Apr. 7, 2009

(54) METHOD FOR IDENTIFYING CONTAMINANTS

(75) Inventors: Paul H. Shelley, Lakewood, WA (US); Diane R. LaRiviere, Seattle, WA (US)

(73) Assignee: The Boeing Company, Chicago, IL (US)

( * ) Notice: Subject to any disclaimer, the term of this patent is extended or adjusted under 35 U.S.C. 154(b) by 926 days.

This patent is subject to a terminal disclaimer.

(21) Appl. No.: 10/720,766

(22) Filed: Nov. 24, 2003

(65) Prior Publication Data

US 2005/0124074 A1 Jun. 9, 2005

(51) Int. Cl.
G01N 24/00 (2006.01)
G01N 21/62 (2006.01)
G01T 1/167 (2006.01)
G01T 1/169 (2006.01)
G01J 5/02 (2006.01)

(52) U.S. Cl. .................. 436/173; 436/171; 250/339.01; 250/301

(58) Field of Classification Search ................. 436/171, 436/173; 250/339.01, 301
See application file for complete search history.

(56) References Cited

U.S. PATENT DOCUMENTS

| | | | |
|---|---|---|---|
| 3,017,512 A | 1/1962 | Wolbert | |
| 3,973,122 A | 8/1976 | Goldberg | |
| 3,994,586 A | 11/1976 | Sharkins et al. | |
| 4,549,079 A | 10/1985 | Terasaka et al. | |
| 4,657,390 A | 4/1987 | Doyle | |
| 4,791,296 A | 12/1988 | Carpio | |
| 4,800,279 A | 1/1989 | Hieftje et al. | |
| 5,015,856 A | 5/1991 | Gold | |
| 5,381,228 A | 1/1995 | Brace | |
| 5,406,082 A * | 4/1995 | Pearson et al. | ......... 250/339.11 |
| 5,714,758 A | 2/1998 | Neu | |
| 5,952,660 A | 9/1999 | Kip et al. | |
| 6,052,191 A | 4/2000 | Brayden, Jr. et al. | |
| 2002/0164651 A1 * | 11/2002 | Steinbeck | ................... 435/7.1 |

FOREIGN PATENT DOCUMENTS

DE 2252527 10/1972

WO WO 01/92820 A1 12/2001

OTHER PUBLICATIONS

Kumar, C. Siva et al., "Studies on anodic oxide coating with low absorptance and high emittance on aluminum alloy 2024," Solar Energy Material & Solar Cells 60 (2000) p. 51-57, Received Feb. 22, 1999, received in revised form Apr. 12, 1999, accepted Jun. 1, 1999, www.elsevier.com.
Kumar, C. Siva et al., "Studies on white anodizing on aluminum alloy for space applications," Applied Surface Science 151 (1999) p. 280-286, Received Mar. 20, 1999, accepted May 31, 1999, www.elsevier.nl/locate/apusc.
Boeing Material Safety Data Sheet (MSDS) No. 088508, revised Jan. 16, 2003, regarding SPRAYLAT, 4 pgs.
Boeing Material Safety Data Sheet (MSDS) No. 099921, revised Apr. 22, 1993, regarding AZTEC, 2 pgs.
Boeing Material Safety Data Sheet (MSDS) No. 21234, revised Jan. 30, 2001, regarding ALKASOL 27, 9 pgs.
Boeing Material Safety Data Sheet (MSDS) No. 28160, revised Jul. 6, 1998, regarding ALODINE 1200, 7 pgs.
Boeing Material Safety Data Sheet (MSDS) No. 55492, revised Apr. 25, 1989, regarding MICROCUT, 4 pgs.
Boeing Material Safety Data Sheet (MSDS) No. 67305, revised Feb. 1, 2000, regarding TEFLON, 3 pgs.
Boeing Material Safety Data Sheet (MSDS) No. 6779, revised Nov. 1, 1991, regarding JET CLEAN E, 4 pgs.
Castrol Product Data Sheet, revised Nov. 30, 2000, regarding Castrol BRAYCOTE 248, 2 pgs.
Chemetall Oakite Material Safety Data Sheet (MSDS), dated Jun. 6, 2003, regarding DINITROL AV 30, 4 pgs.
Orelube Corporation Material Safety Data Sheet (MSDS), prepared Mar. 20, 2003, regarding BOELUBE, 2 pgs.
Swagelok Material Safety Data Sheet (MSDS), revised Jan. 2003, regarding SNOOP, 4 pgs.
Univar USA Material Safety Data Sheet (MSDS) No. P22400VS, issued Nov. 2, 1997, regarding DINITROL AV 8, 3 pgs.
Univar USA Material Safety Data Sheet (MSDS) No. P21621VS, issued Jan. 8, 1997, regarding PACE B-82, 3 pgs.

* cited by examiner

*Primary Examiner*—Jill Warden
*Assistant Examiner*—Keri A Moss

(57) ABSTRACT

A method is provided for identifying contaminants on a surface. In one embodiment, an infrared beam is transmitted onto a sample. A first infrared absorbance of the sample is determined at a first wave number. A second infrared absorbance of the sample is determined at a second wave number. The first absorbance is correlated to a first absorbance peak of a contaminant. The presence of a predetermined level of the contaminant is confirmed by correlating the second infrared absorbance to a second absorbance peak of the contaminant.

160 Claims, 37 Drawing Sheets

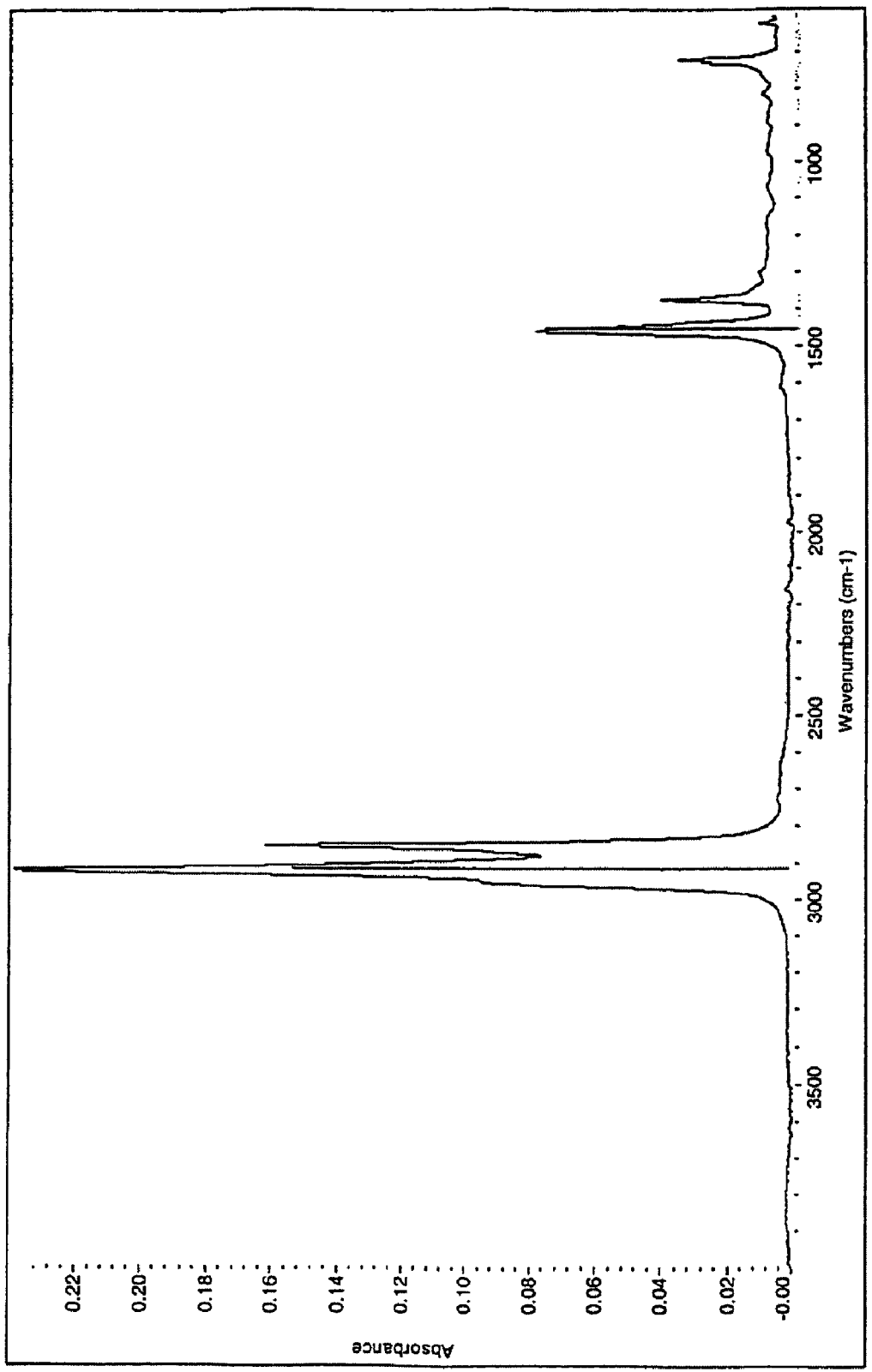
fig. 8  Corrosion Inhibiting Compounds (CICs) – Braycote 248

Lanolin

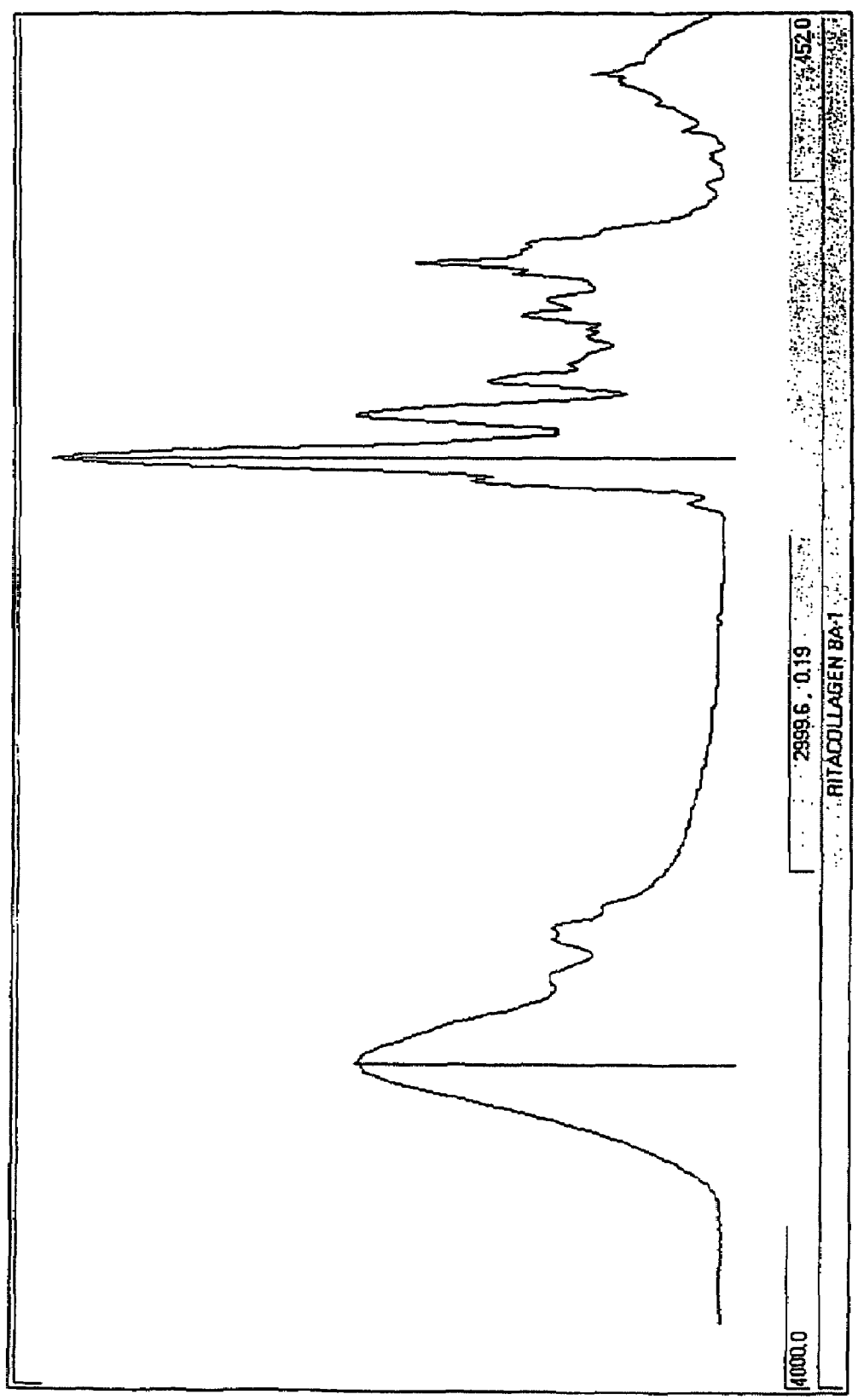
fig. 22B  Proteins - Collagen

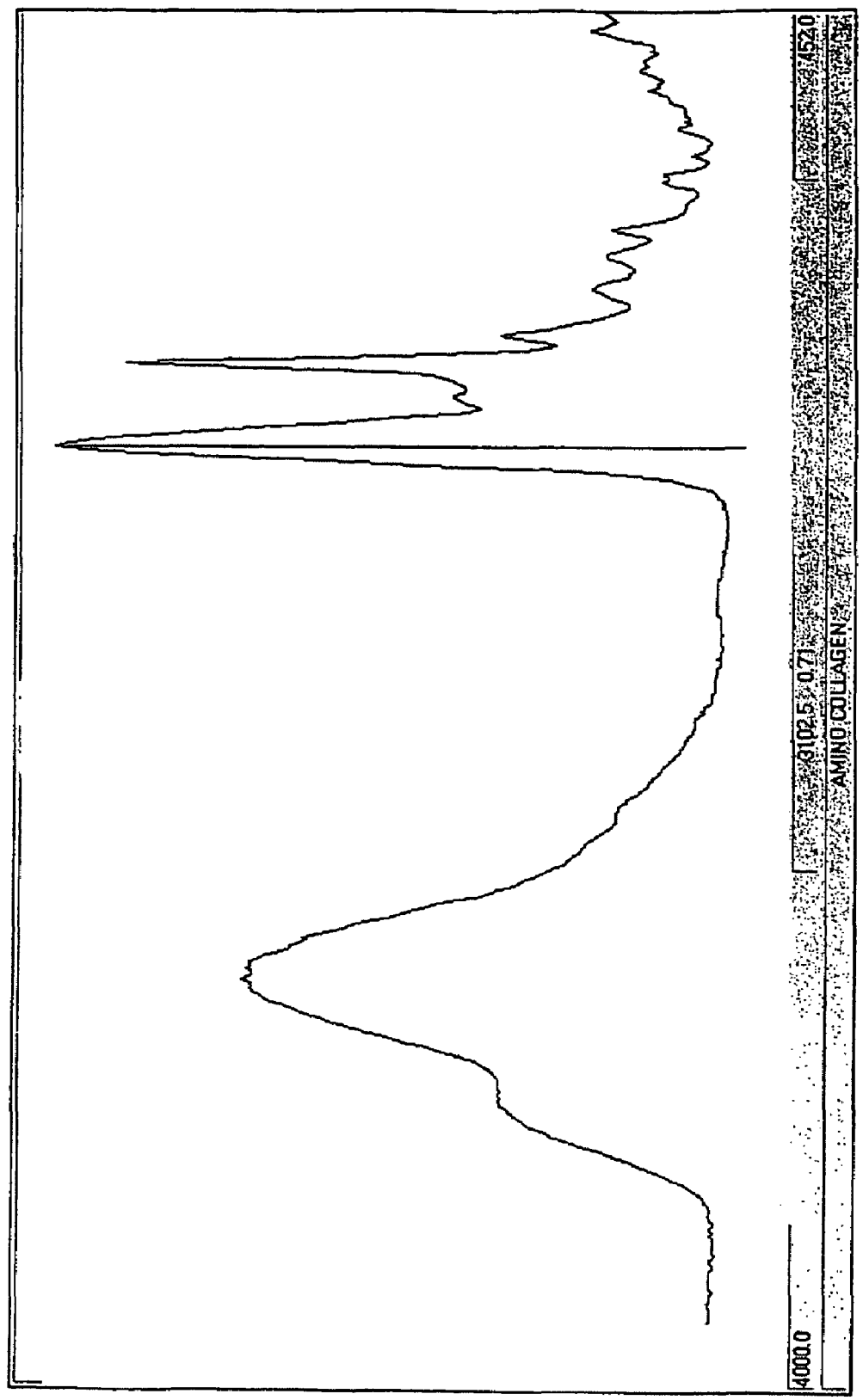
fig. 22C  Proteins - Collagen

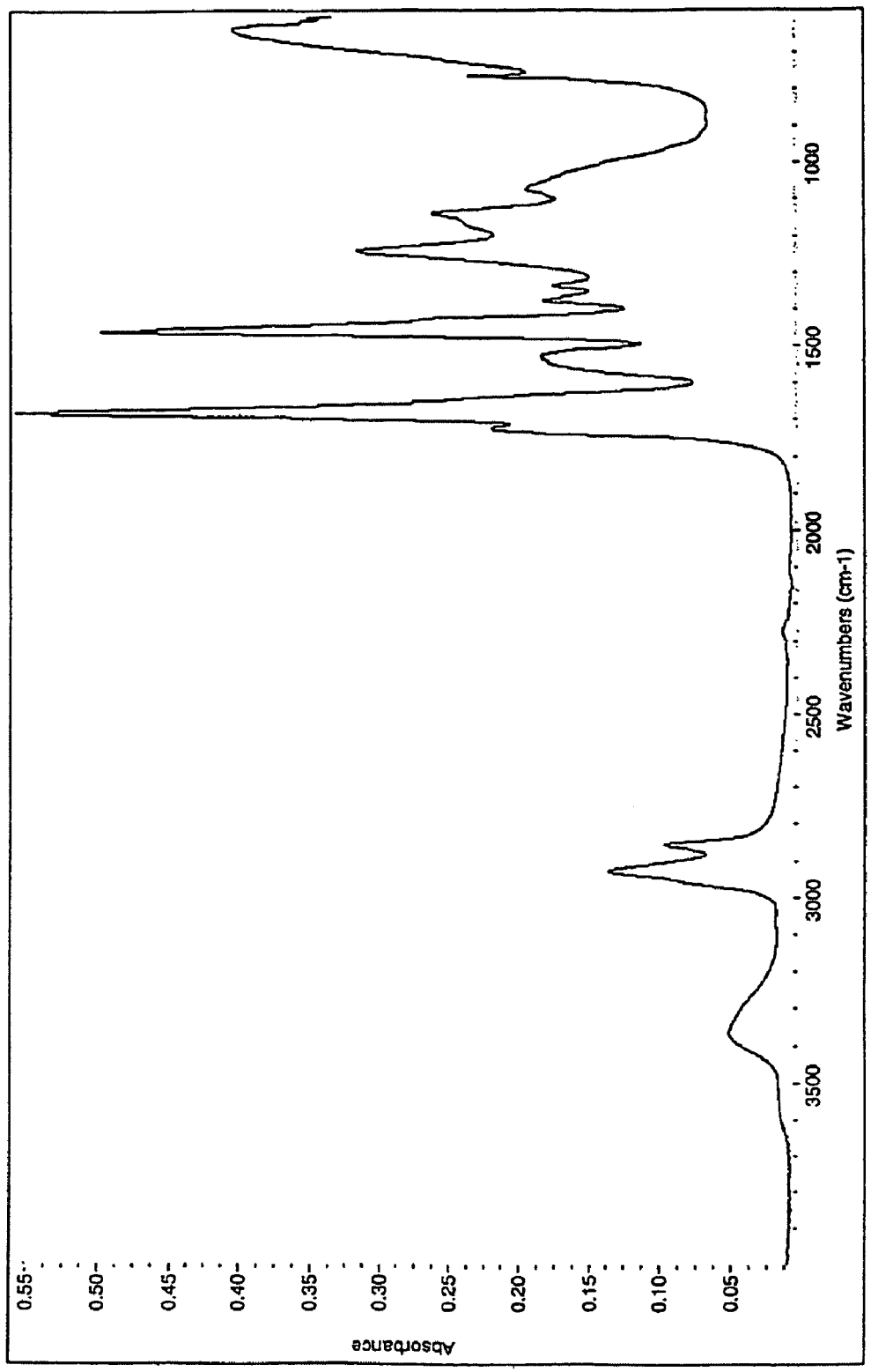
fig. 23B  Paint – Topcoat BMS 10-72 (white-eclipse)

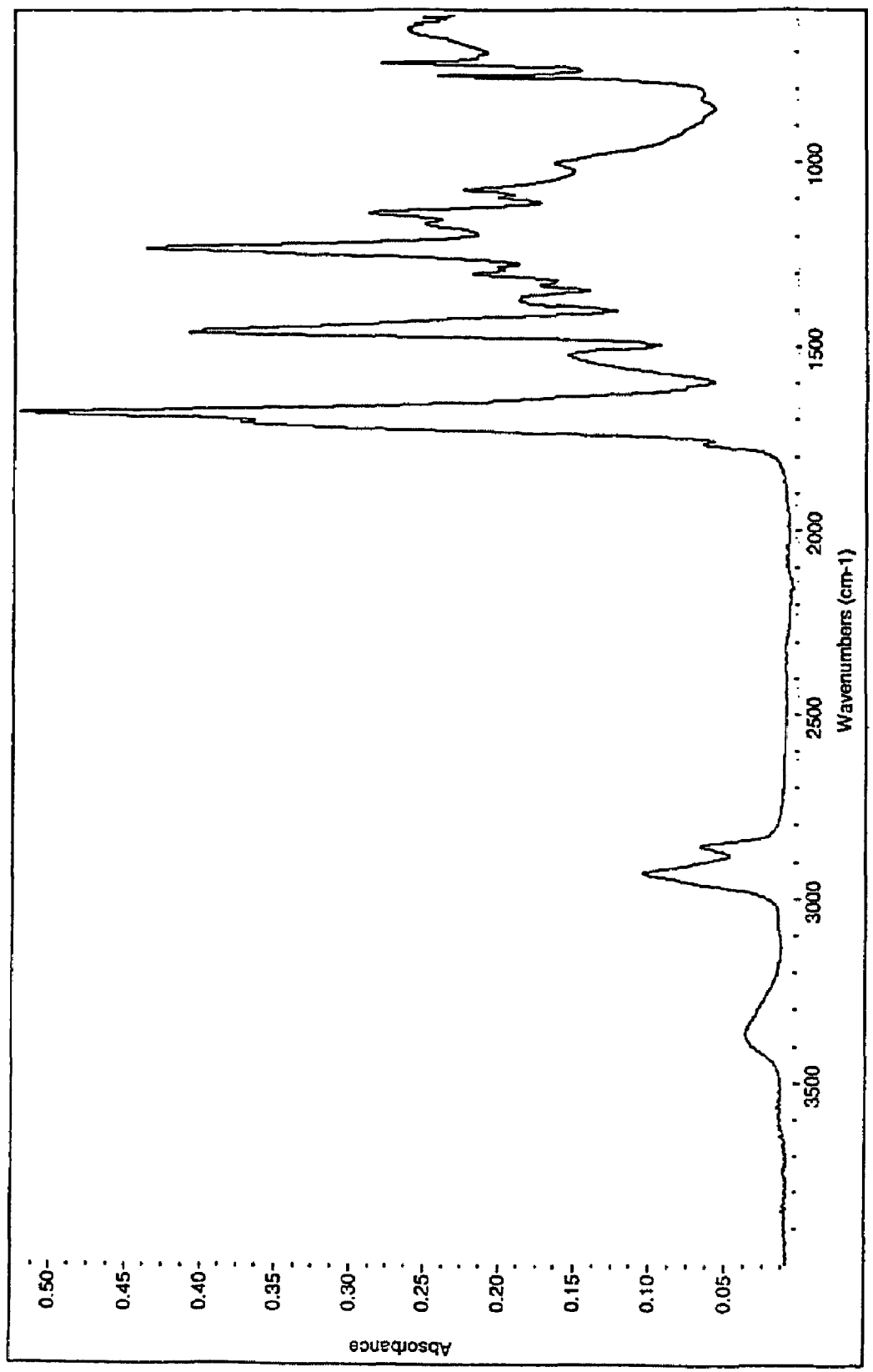
fig. 23D  Paint – Topcoat BMS 10-72 (gray P-1100)

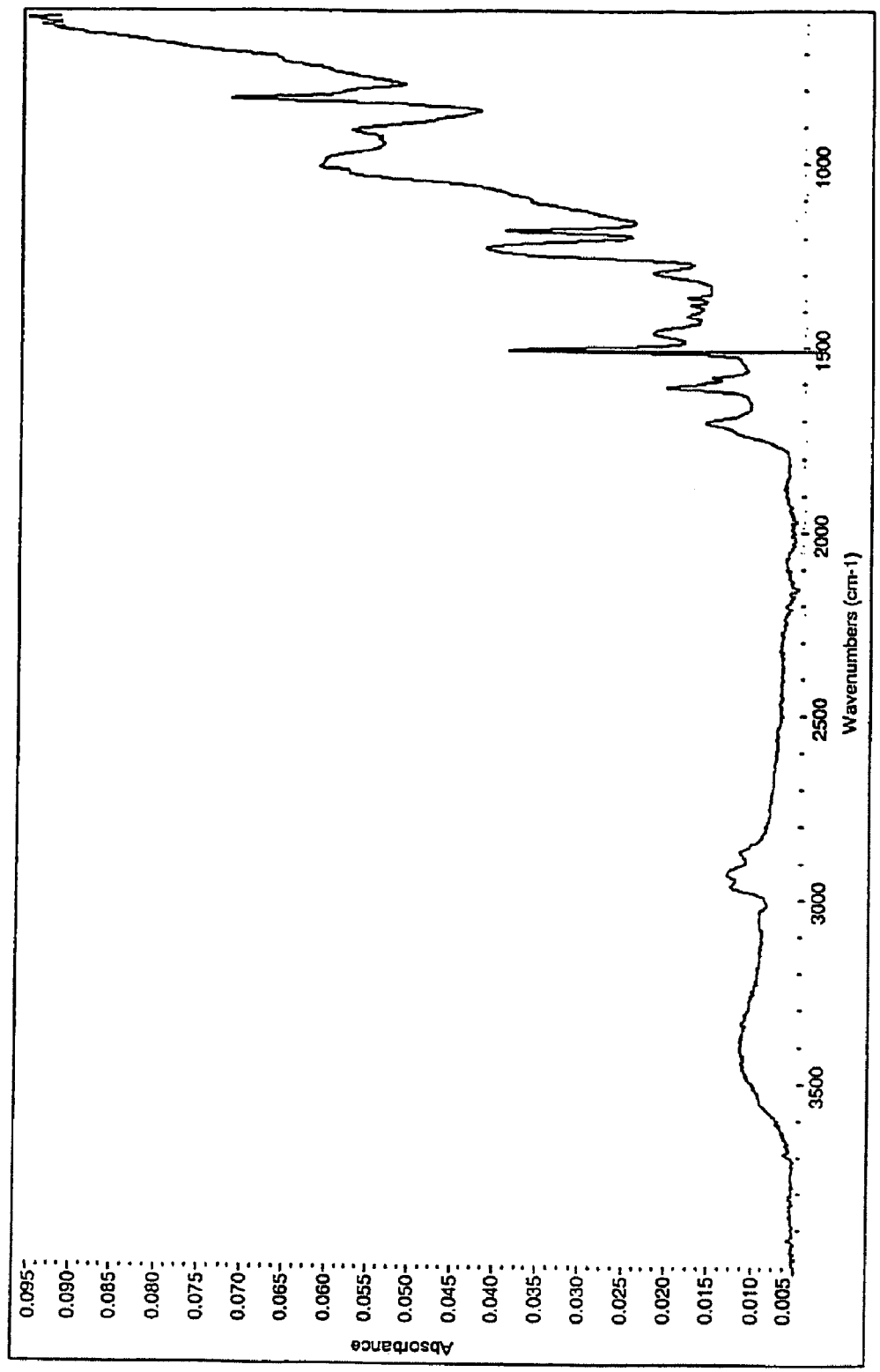
fig. 24C  Paint – Primer BMS 10-20

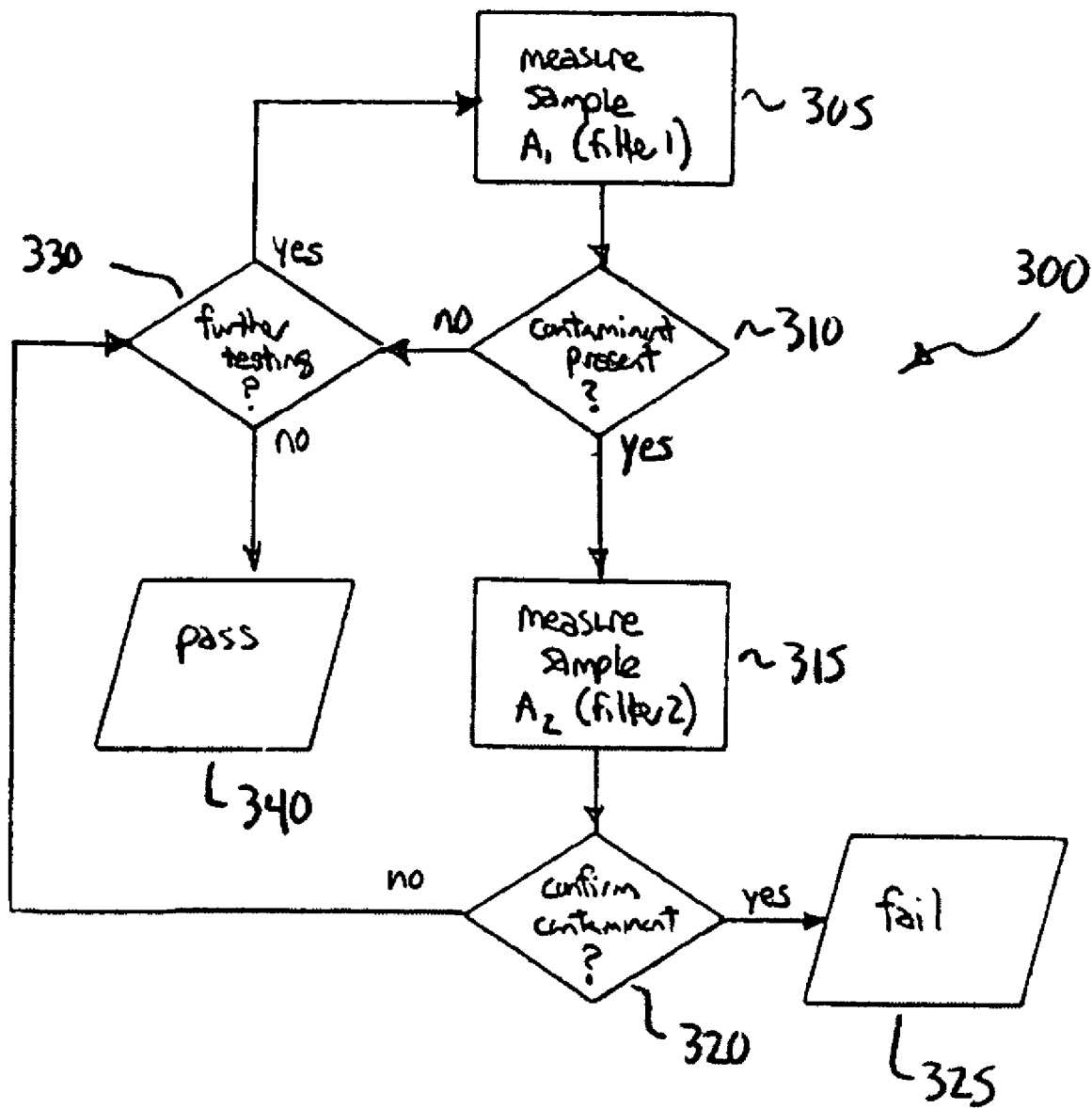

METHOD FOR IDENTIFYING CONTAMINANTS

FIELD OF THE INVENTION

This invention relates generally to measurement and, more specifically, to measurement of surface contamination.

BACKGROUND OF THE INVENTION

During processing of a material, detecting presence of a contaminant on a surface of the material or identifying a contaminant on the surface of the material may be desired. For example, when painting, priming, or sealing a surface, verification of surface cleanliness is useful to assure adequate adhesion between the paint, primer, or sealant and the surface.

Known surface contamination detection methods now available include portable Fourier Transform Infrared (FT-IR) spectrometers, but these methods utilize heavy and bulky equipment. Surface contamination detection with currently known FT-IR systems requires expert interpretation and, often, detailed knowledge of system software and hardware.

Therefore, there exists an unmet need in the art for a simple and reliable method of detecting and identifying surface contamination.

SUMMARY OF THE INVENTION

The present invention provides a non-destructive method for efficiently and objectively determining the presence and nature of a contaminant on a substrate or sample. The invention may be utilized to determine whether manufacturing surfaces are ready for applying coatings.

According to one embodiment of the present invention, a value $I_s$ of infrared energy reflected by a substrate is determined at at least two wave members. A contaminant is then identified on the surface by correlating the value $I_s$ of infrared energy reflected to the contaminant.

According to an aspect of the invention, an infrared beam is transmitted onto a sample. A first infrared absorbance of the sample is determined at a first wave number. A second infrared absorbance of the sample is determined at a second wave number. The first absorbance is correlated to a first absorbance peak of a contaminant. The presence of a predetermined level of the contaminant is confirmed by correlating the second infrared absorbance to a second absorbance peak of the contaminant.

BRIEF DESCRIPTION OF THE DRAWINGS

The preferred and alternative embodiments of the present invention are described in detail below with reference to the following drawings.

FIG. 3D is a graph of infrared absorbance of an exemplary grease BMS 3-34;

As shown in FIG. 5, this lubricant has identifiable absorbance peaks at 1071 cm−1, and at 3279 cm−1, that suitably differentiate this lubricant from other common manufacturing contaminants.

Corrosion inhibiting compounds may also be detected and identified utilizing the method of the present invention.

Figure 6:
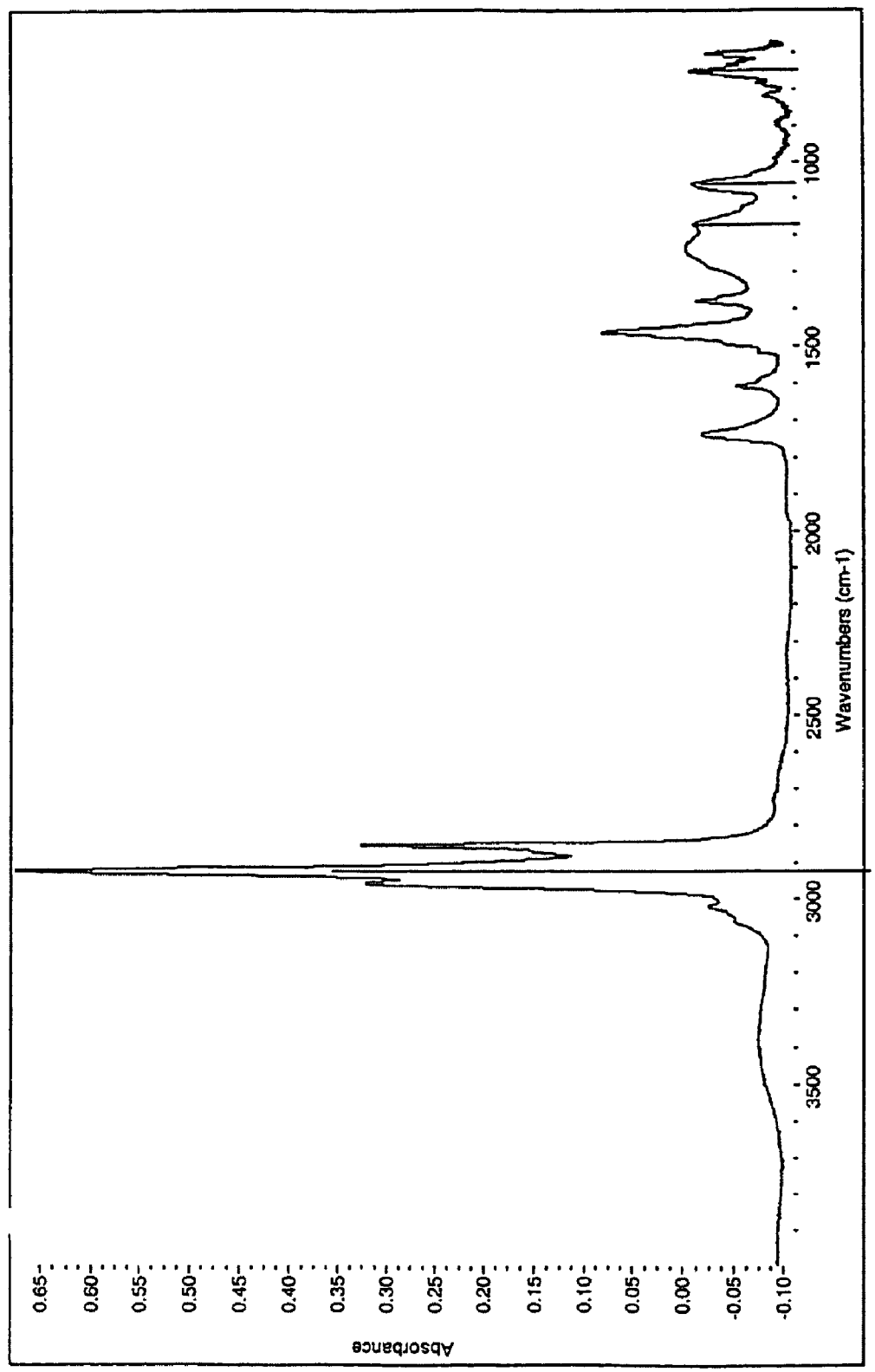

FIG. 6 is a graph of infrared absorbance of an exemplary corrosion inhibiting compound, DINITROL® AV30, manufactured by Dinol International, as described in the Chemetall Oakite Material Safety Data Sheet (MSDS) dated Jun. 6, 2003, the content of which is hereby incorporated by reference. DINITROL® AV30 has identifiable absorbance peaks at 2,924 cm−1 and at 1,060 cm−1.

Figure 7:
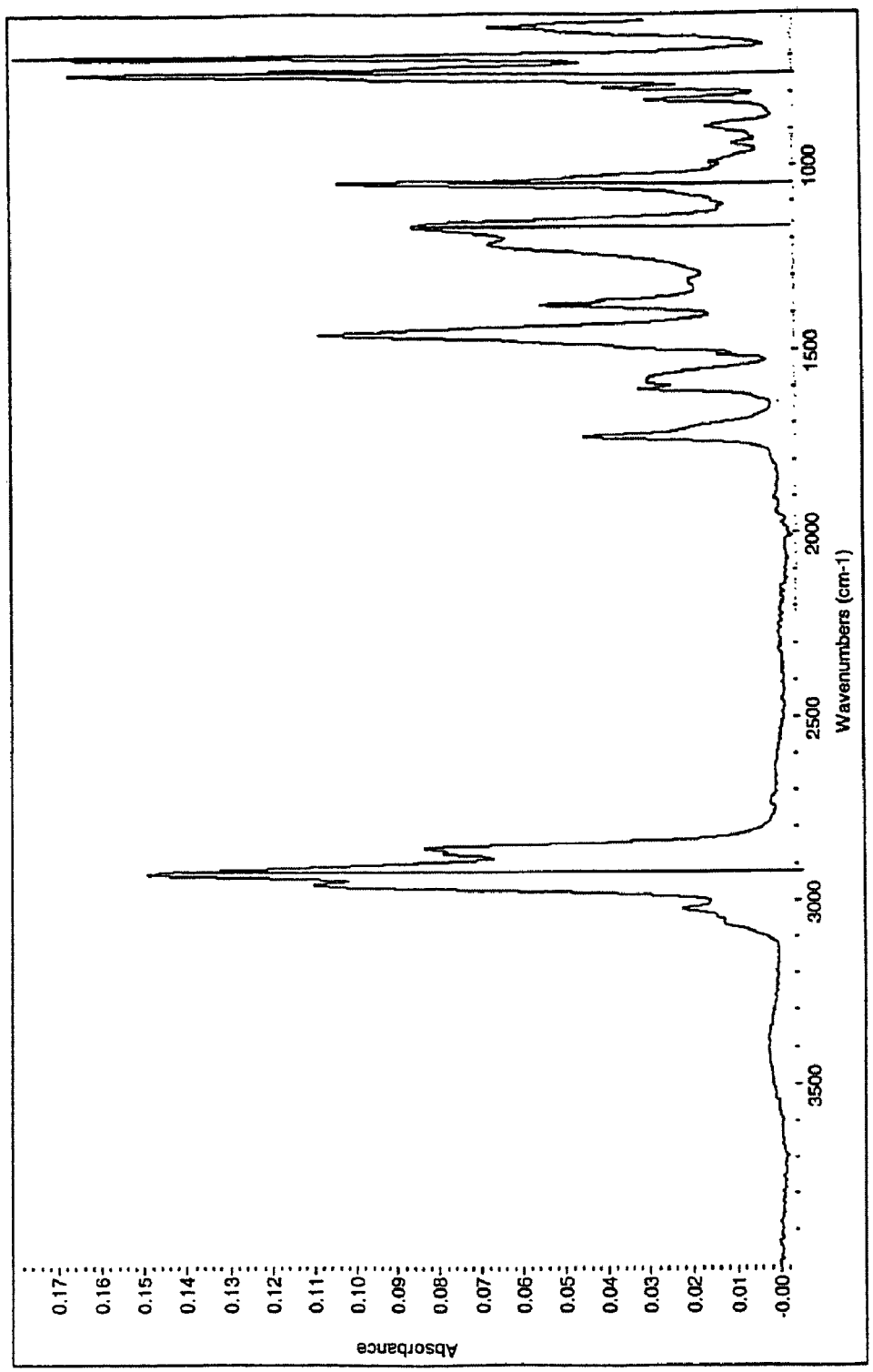
Figure 5:
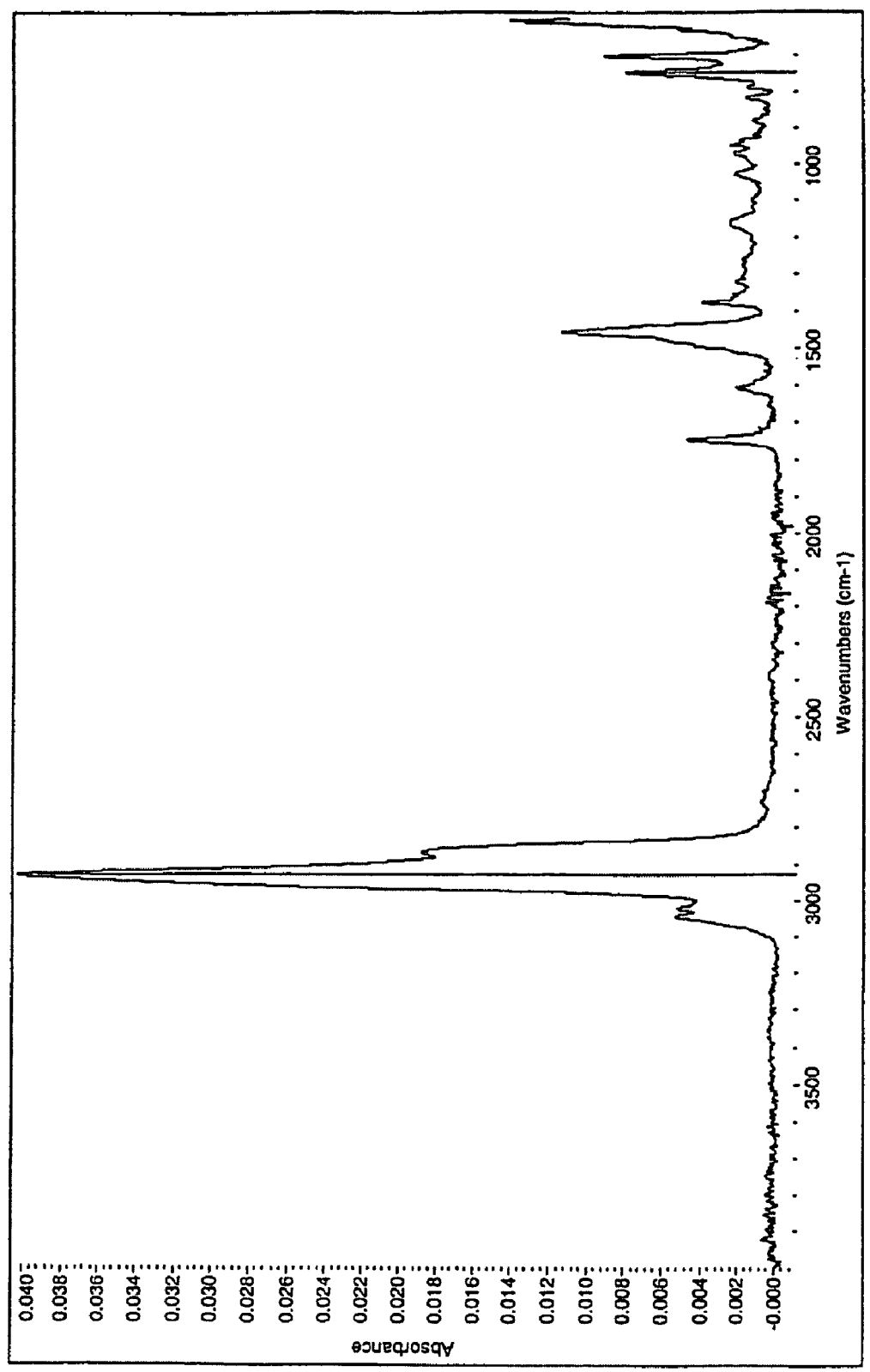

FIG. 7 is a graph of infrared absorbance of an exemplary corrosion inhibiting compound, DINITROL® AV8, manufactured by Dinol International, as described in Univar USA Material Safety Data Sheet (MSDS) No. P22400VS, issued on Nov. 2, 1997, the content of which is hereby incorporated by reference. DINITROL® AV8 has identifiable absorbance peaks at 2,924 cm−1 and at 752 cm−1.

FIG. 8 is a graph of infrared absorbance of an exemplary corrosion inhibiting compound, BRAYCOTE® 248, manufactured by Castrol, Inc, as described in the Castrol Product Data Sheet revised on Nov. 30, 2000, the content of which is hereby incorporated by reference. BRAYCOTE® 248 has identifiable absorbance peaks at 2,924 cm−1 and at 1,460 cm−1.

FIG. 9 is a graph of infrared absorbance of an exemplary corrosion inhibiting compound, CORBAN™, manufactured by Zip Chem Products. CORBAN™ has identifiable absorbance peaks at 2,924 cm−1 and at 752 cm−1.

Figure 10:
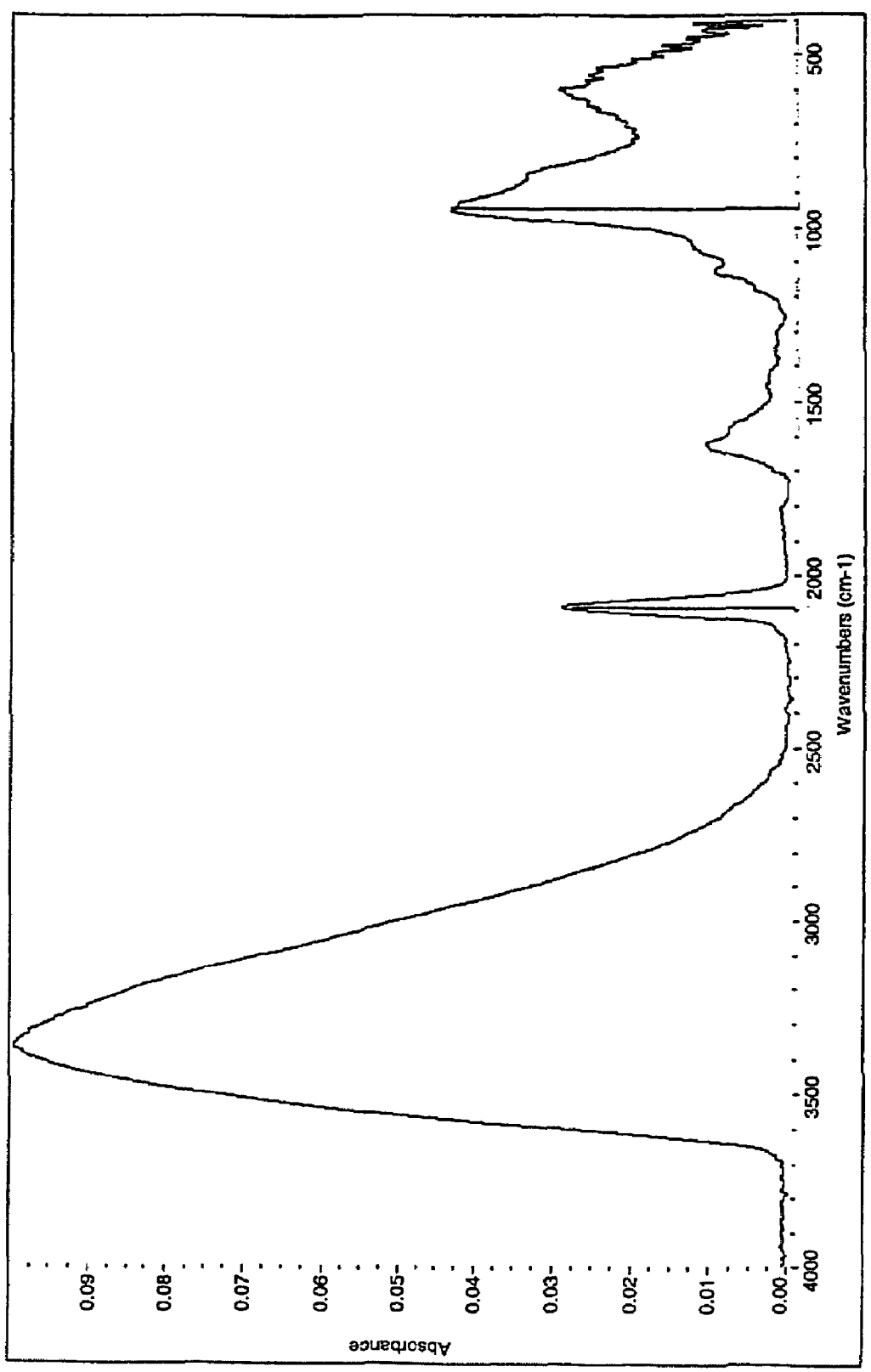

FIG. 10 is a graph of infrared absorbance of exemplary chromate conversion coating Converted ALODINE® 1200, manufactured by Henkel Surface Technologies, as described in Boeing Material Safety Data Sheet (MSDS) No. 28160, revised Jul. 6. 1998, the content of which is hereby incorporated by reference. ALODINE® 1200 has identifiable absorbance peaks at 925 cm−1 and 2,190 cm−1.

Cleaners and soaps also may be identified as a contaminant using a method of the present invention.

Figure 11:
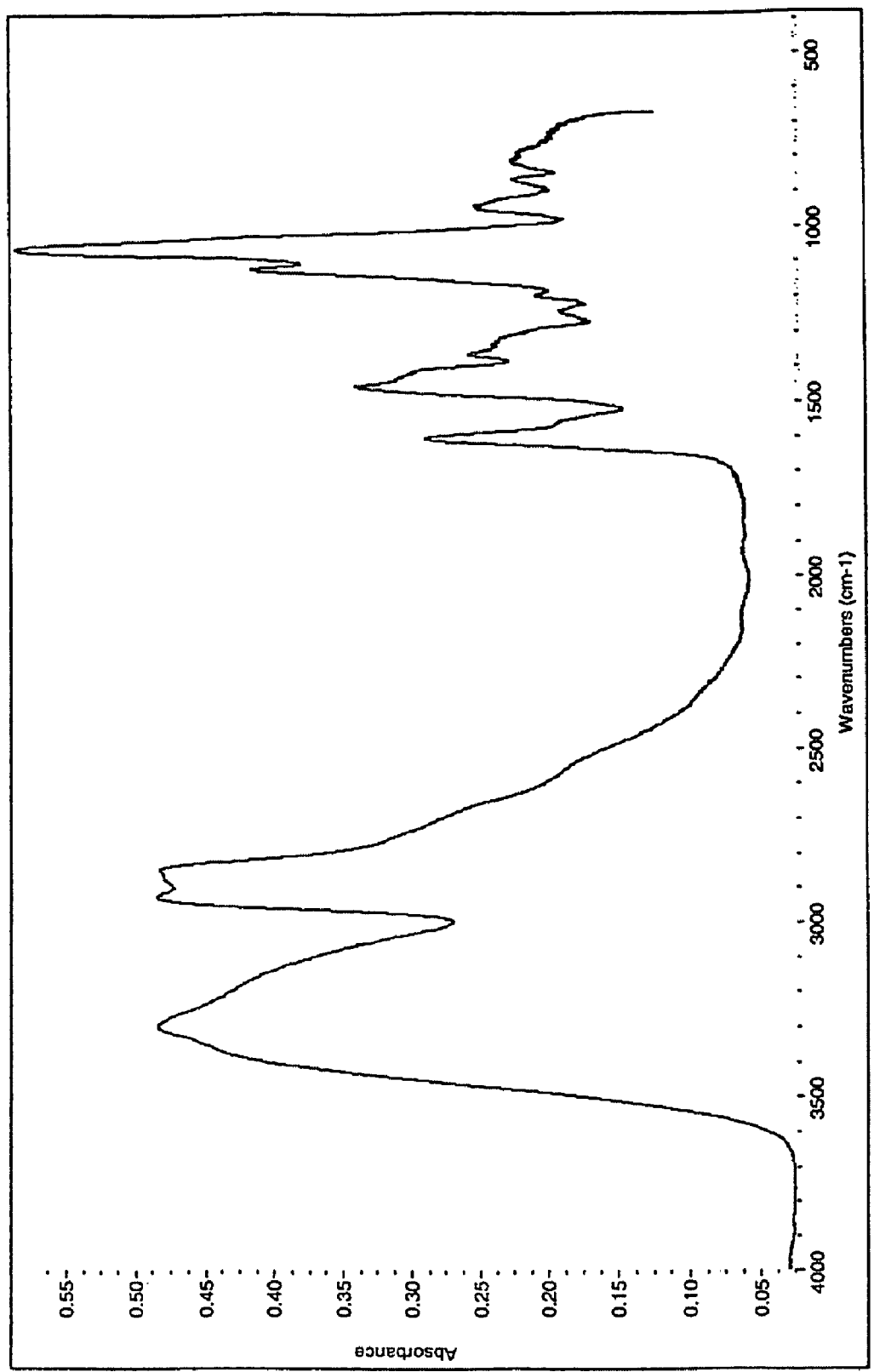

FIG. 11 is a graph of infrared absorbance of an exemplary cleaner/soap, ALKASOL 27, as described in Boeing Material Safety Data Sheet (MSDS) No. 21234, revised Jan. 30, 2001, the content of which is hereby incorporated by reference. ALKASOL 27 has identifiable absorbance peaks at 1,060 cm−1 and at 1,600 cm−1.

Figure 12:
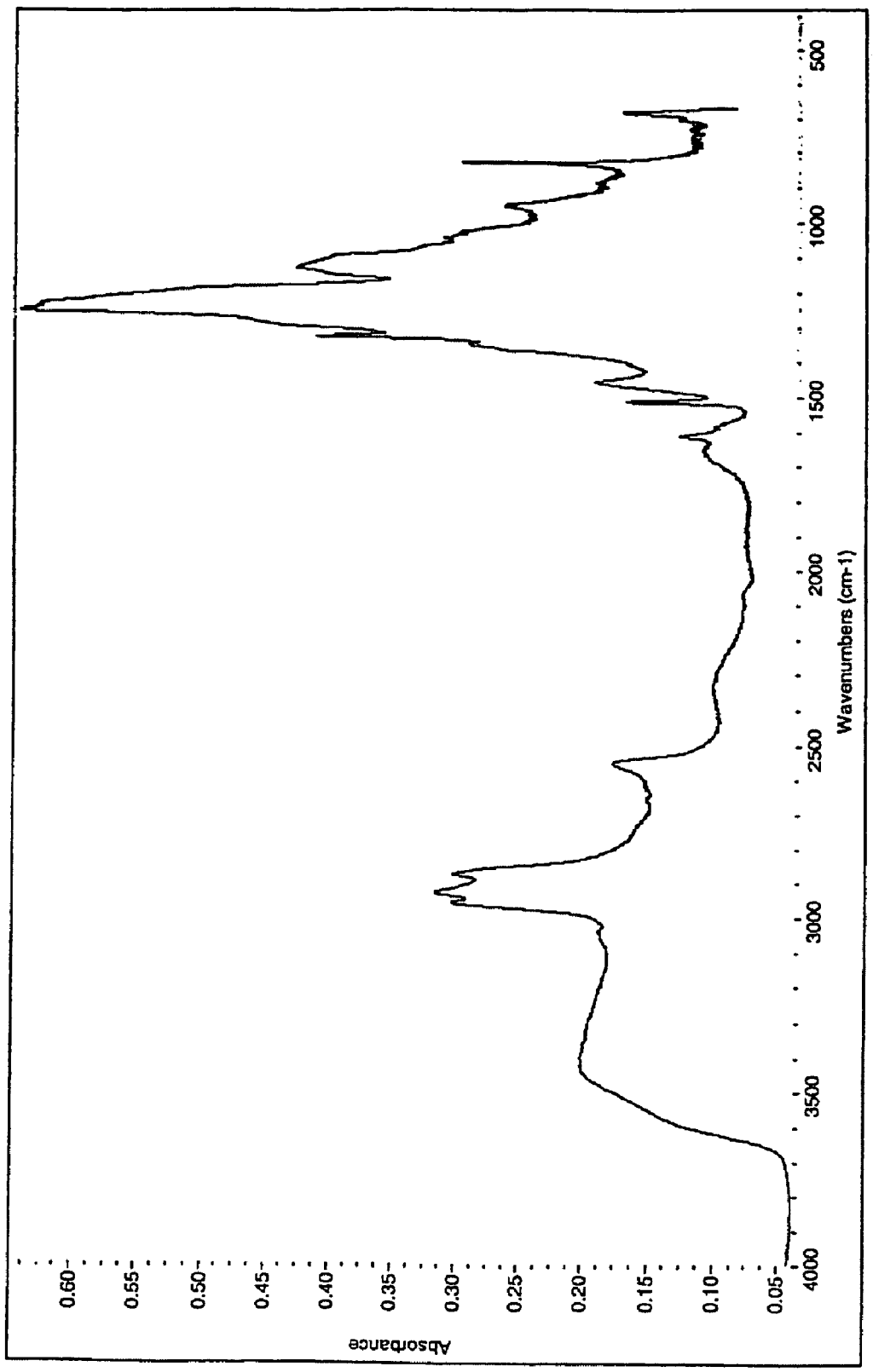

FIG. 12 is a graph of infrared absorbance of an exemplary cleaner/soap, JET CLEAN E manufactured by Melrose Chemicals Limited, as described in Boeing Material Safety Data Sheet (MSDS) No. 6779, revised Nov. 1, 1991, the content of which is hereby incorporated by reference. JET CLEAN E has identifiable absorbance peaks at 1,241 cm−1 and at 2,551 cm−1.

Figure 13:
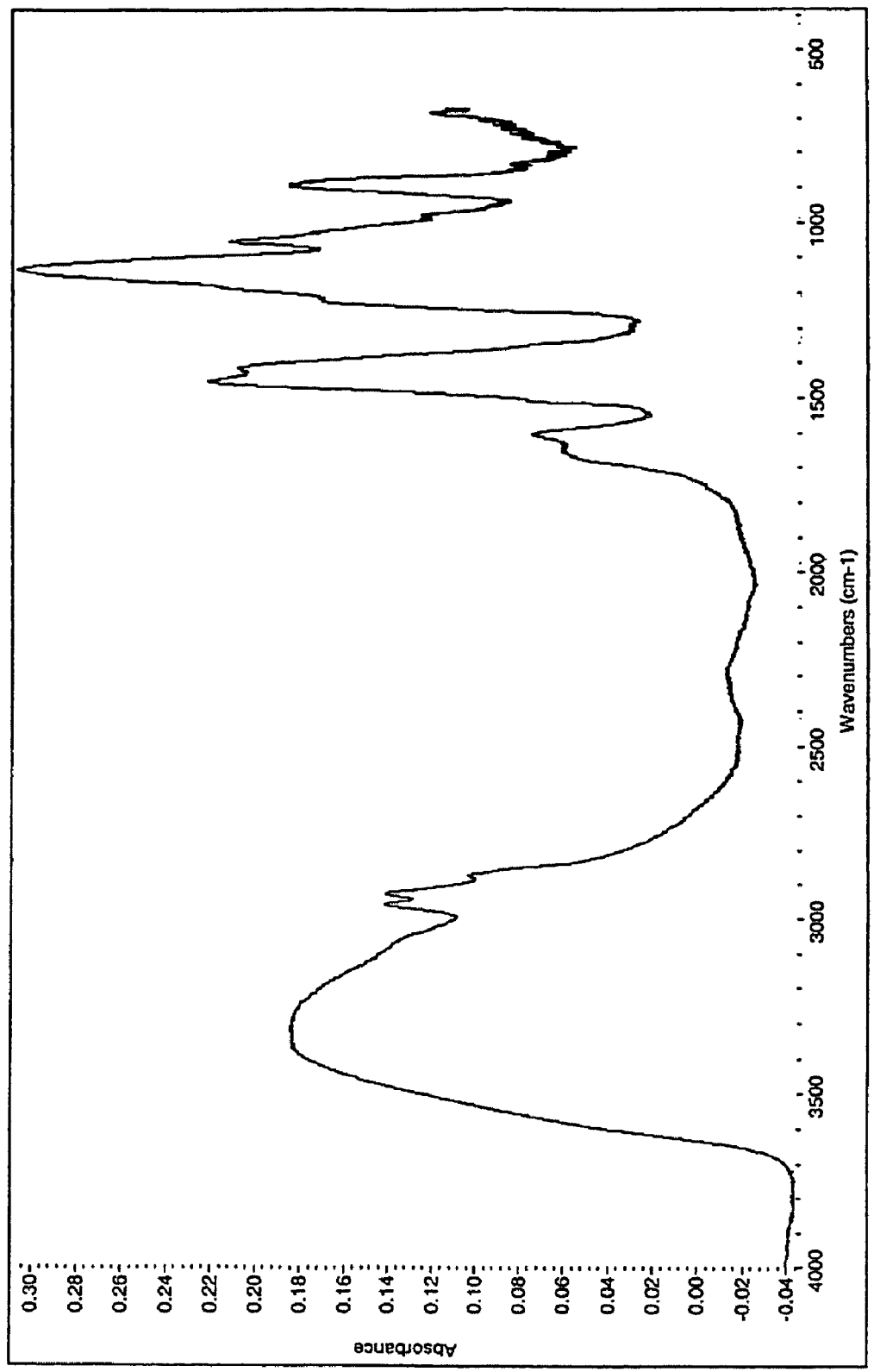

FIG. 13 is a graph of infrared absorbance of an exemplary cleaner/soap, PACE B82, as described in the Univar USA Material Safety Data Sheet (MSDS) No. P21621VS, issued on Jan. 8, 1997, the content of which is hereby incorporated by reference. PACE B82 has identifiable absorbance peak at 1120 cm−1 and at 901 cm−1.

Figure 14:
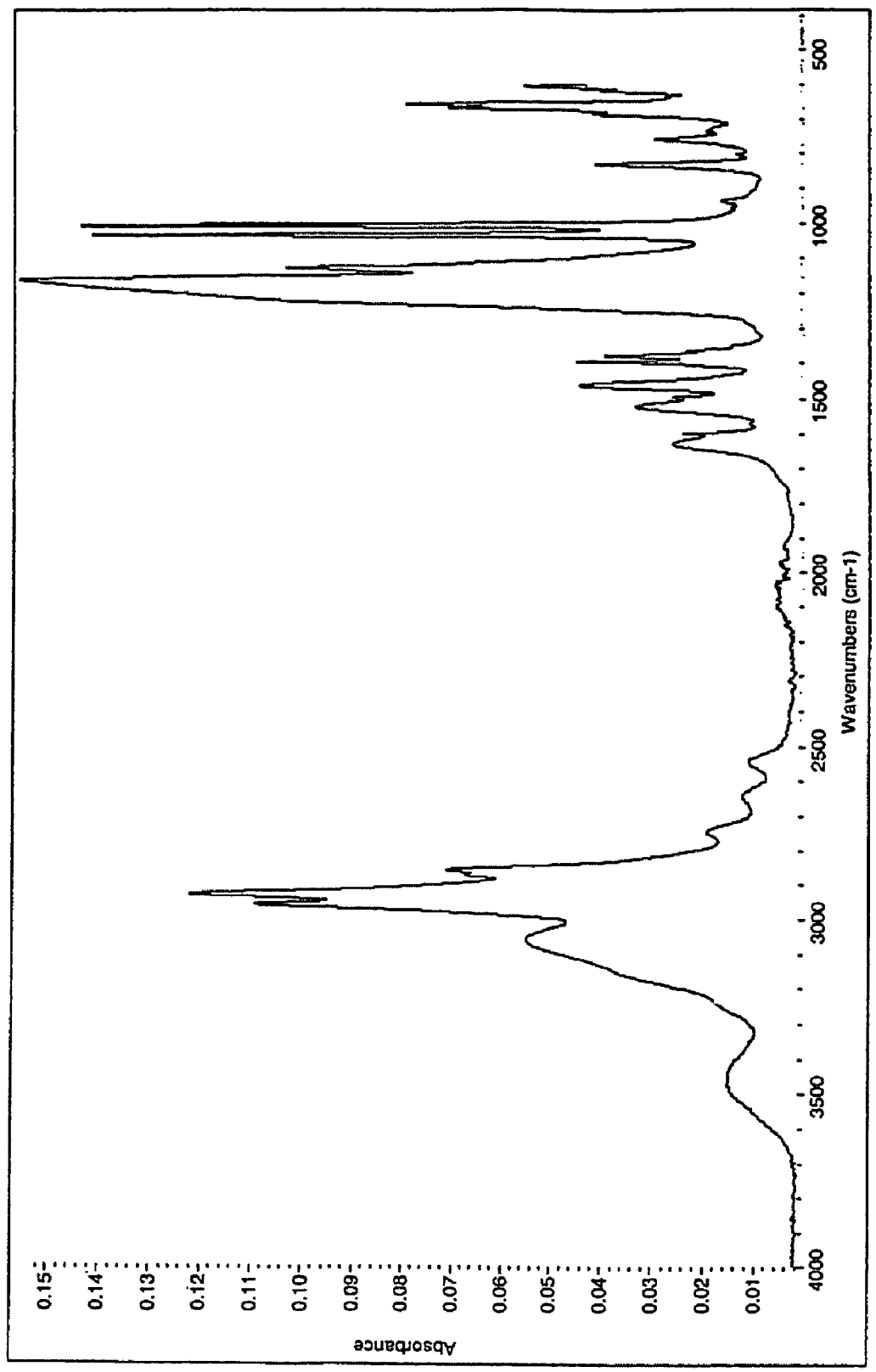

FIG. 14 is a graph of infrared absorbance of an exemplary cleaner/soap, SNOOP®, as described in the Swagelok Material Safety Data Sheet (MSDS) revised in January 2003, the content of which is hereby incorporated by reference. SNOOP® has identifiable absorbance peaks at 1,180 cm−1 and at 1,620 cm−1.

Figure 15:
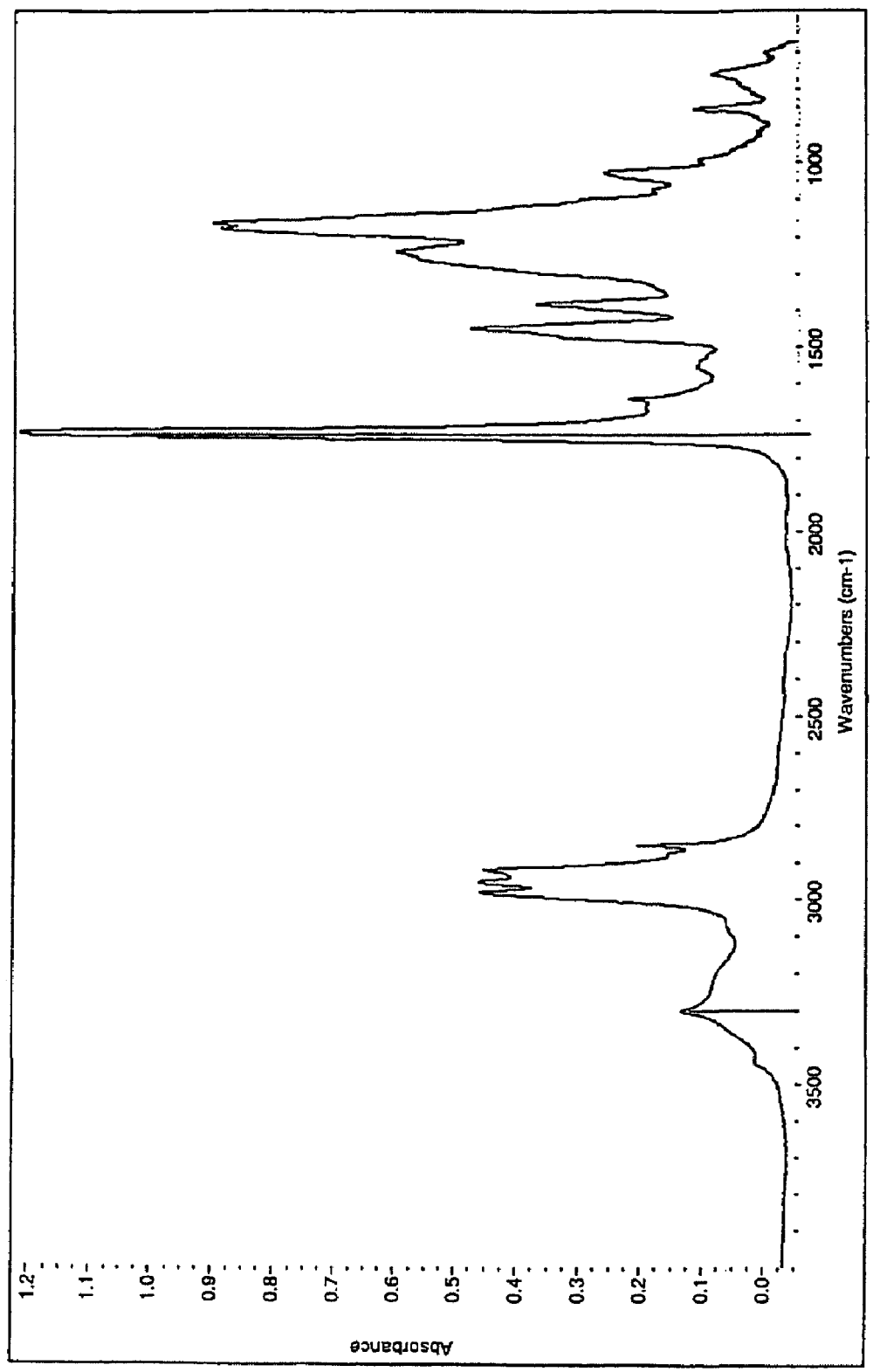

FIG. 15 is a graph of infrared absorbance of an exemplary temporary protective coating used in manufacturing, SPRAYLAT manufactured by Spraylat Corporation, as described in Boeing Material Safety Data Sheet (MSDS) No. 088508, revised Jan. 16, 2003, the content of which is hereby incorporated by reference. SPRAYLAT has been found to have identifiable absorbance peaks at 1730 cm−1 and 3300 cm−1 to differentiate from other common manufacturing contaminants.

Figure 16:
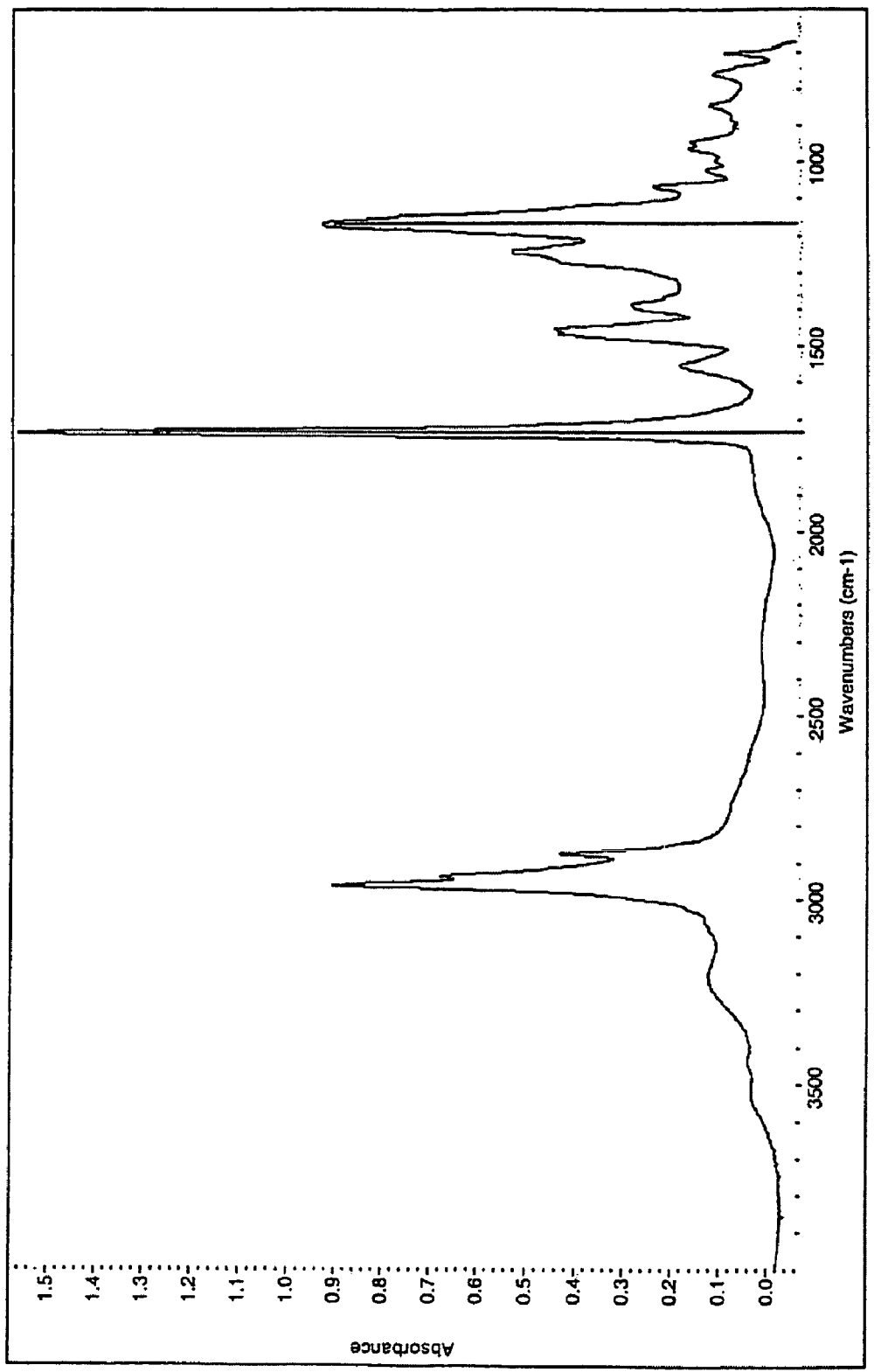

FIG. 16 is a graph of infrared absorbance of an exemplary temporary protective coating used in manufacturing, AZTEC, as described in Boeing Material Safety Data Sheet (MSDS) No. 099921, revised Apr. 22, 1993, the content of which is hereby incorporated by reference. AZTEC has been found to have identifiable absorbance peaks at 1730 cm−1 and 1160 cm−1 to differentiate from other common manufacturing contaminants.

Figure 17:
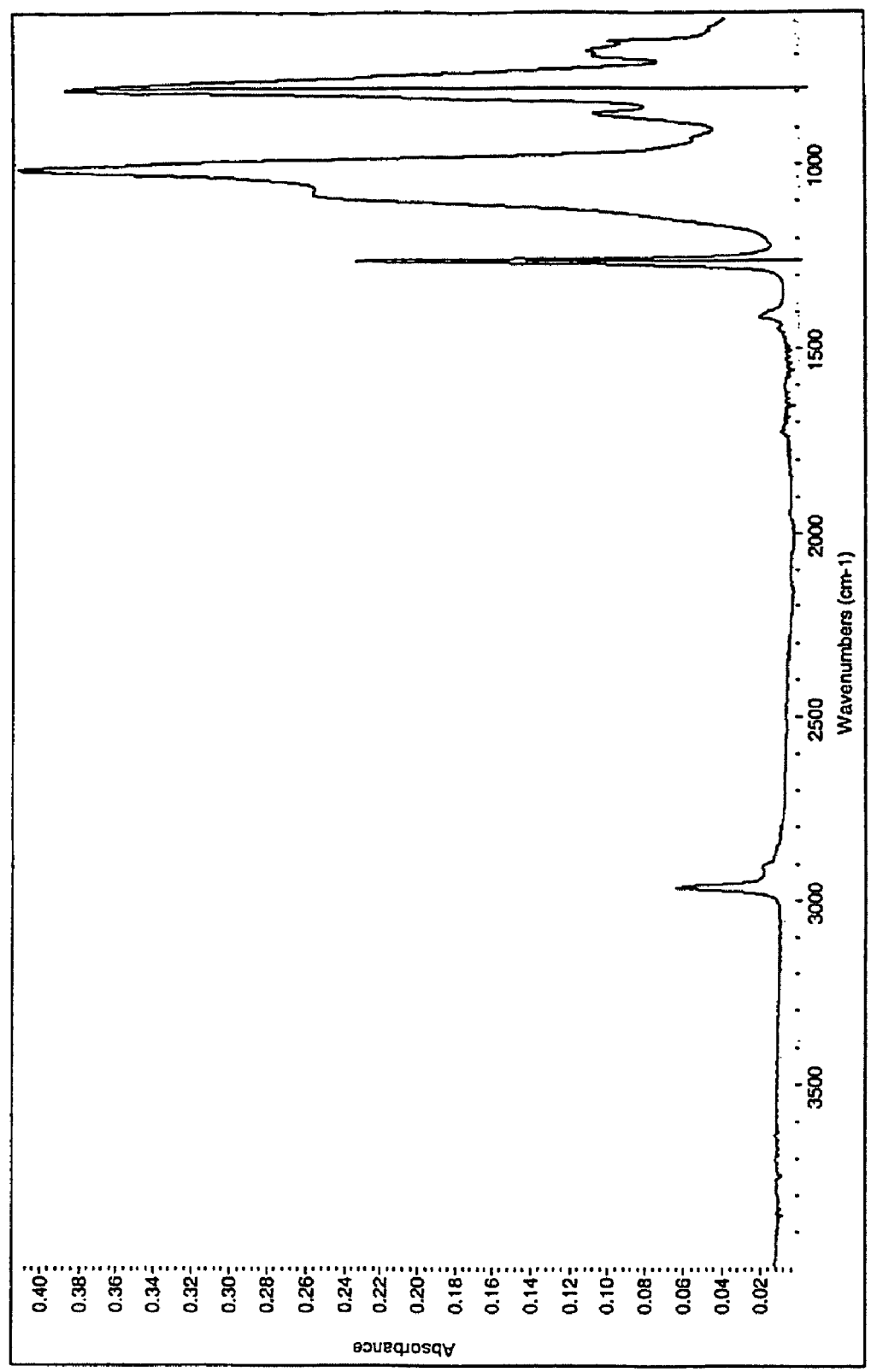

FIG. 17 is a graph of infrared absorbance of an exemplary form release agent, a silicone oil FREKOTE®, manufactured by Loctite Corporation. Release agents are used when forming plastics or epoxy fiber composites to prevent the material from sticking to a form. Silicone oil has been found to have identifiable absorbance peaks at 1259 cm−1 and 800 cm−1.

Figure 18:
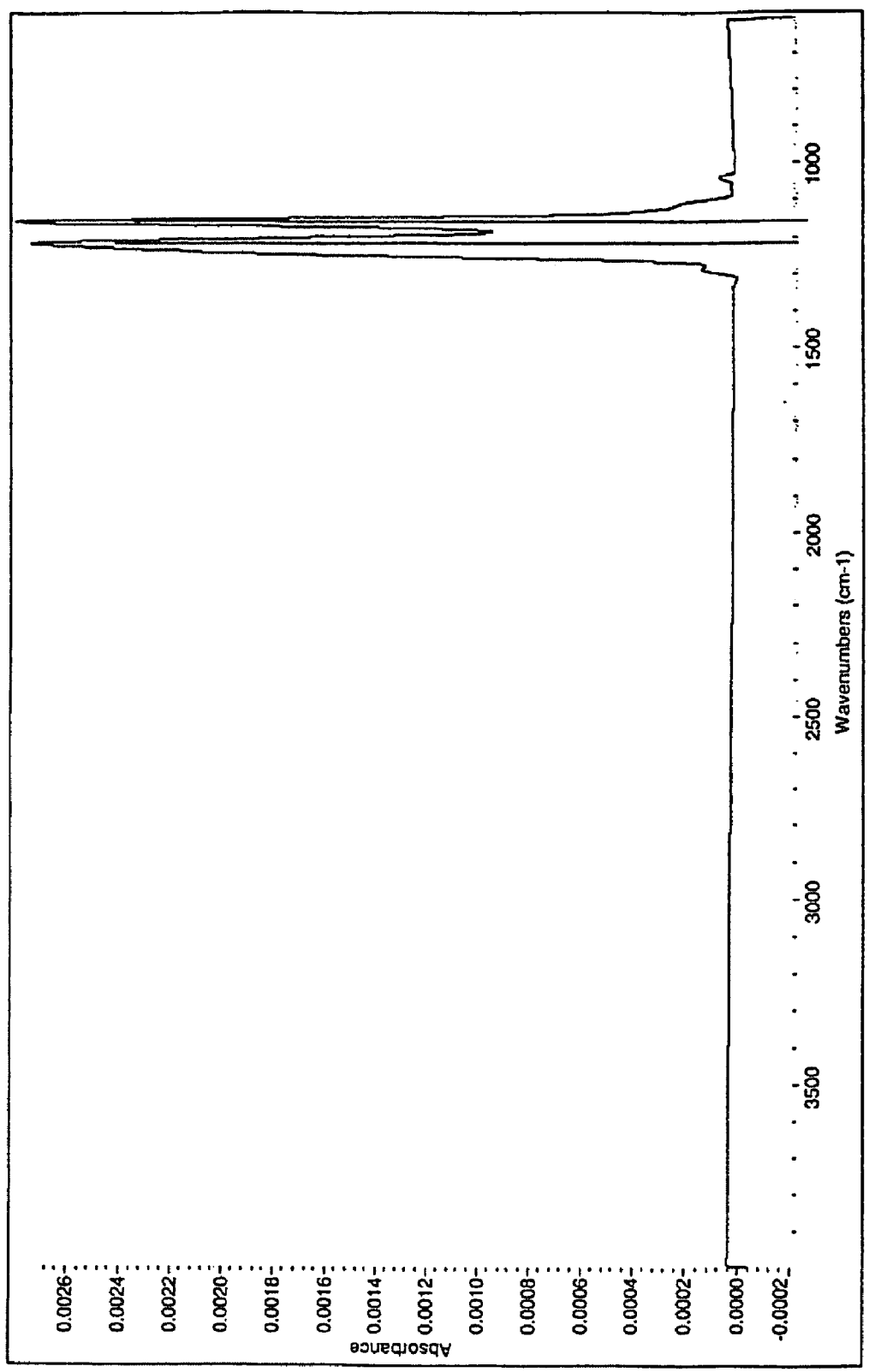

FIG. 18 is a graph of infrared absorbance of an alternate exemplary form release agent, TEFLON®, as described in Boeing Material Safety Data Sheet (MSDS) No. 67305, revised Feb. 1, 2000, the content of which is hereby incorporated by reference. TEFLON® has been found to have identifiable absorbance peaks at 1212 cm−1 and 1155 cm−1.

Figure 19:
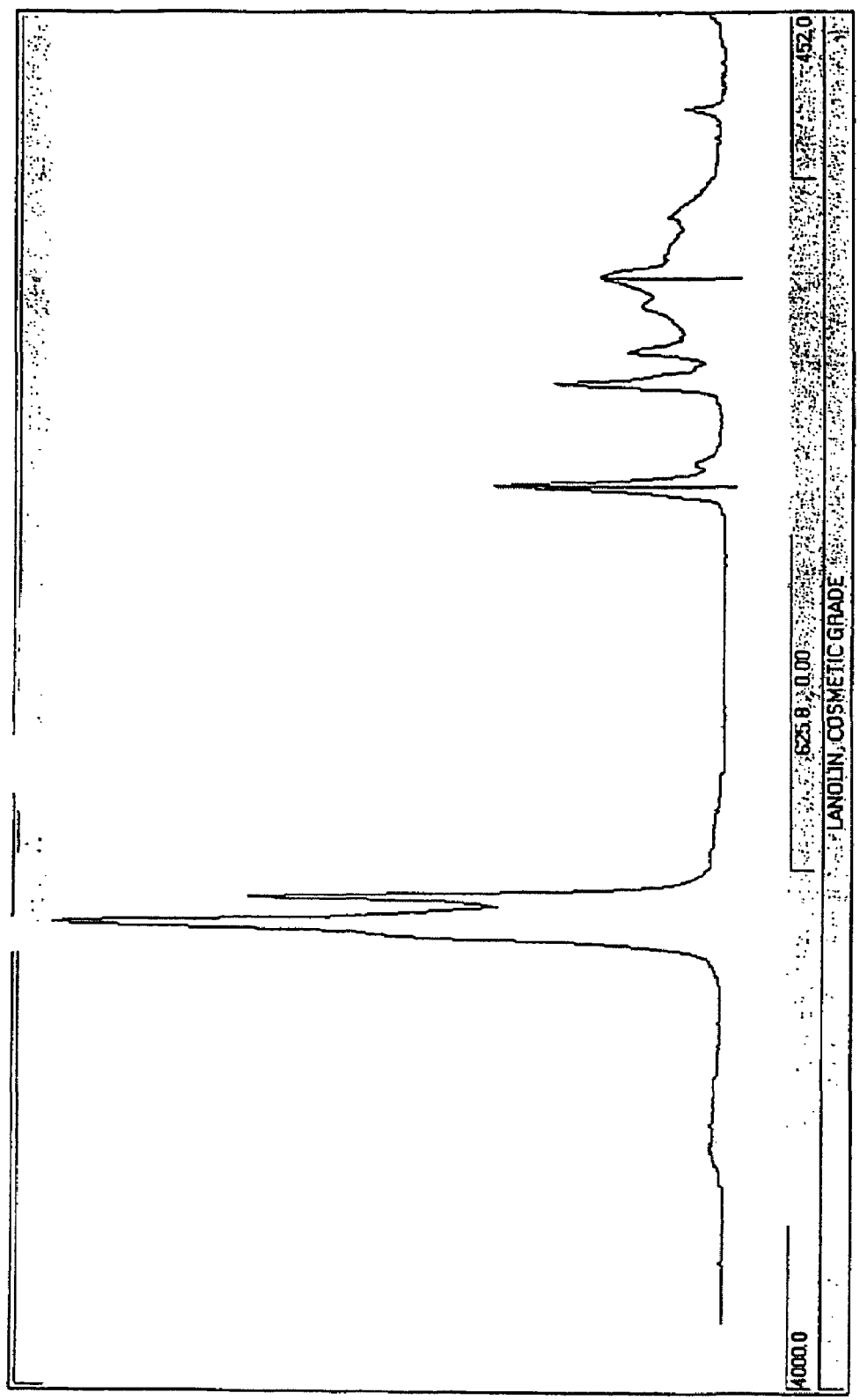
Figure 20:
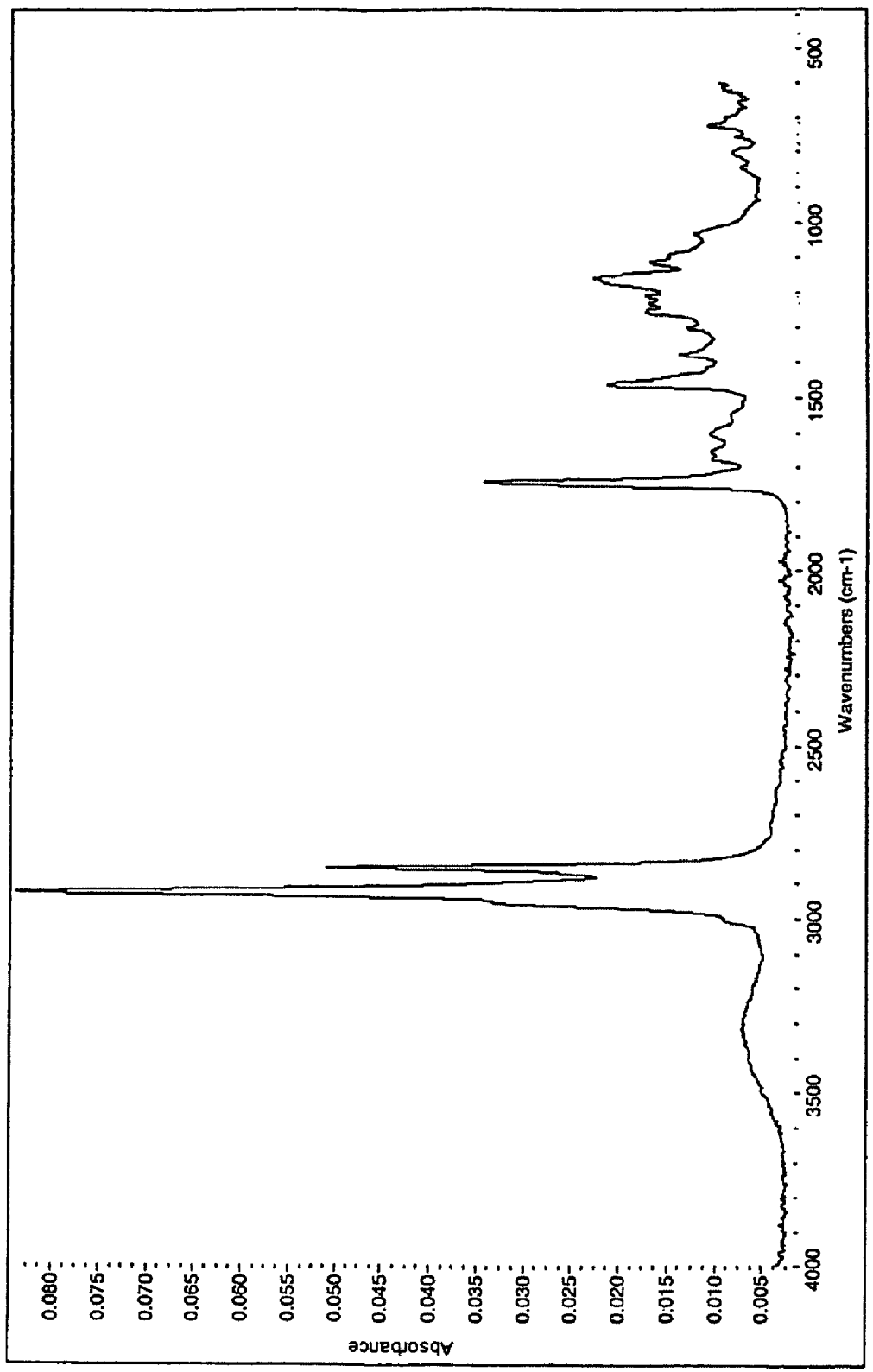
Figure 21:
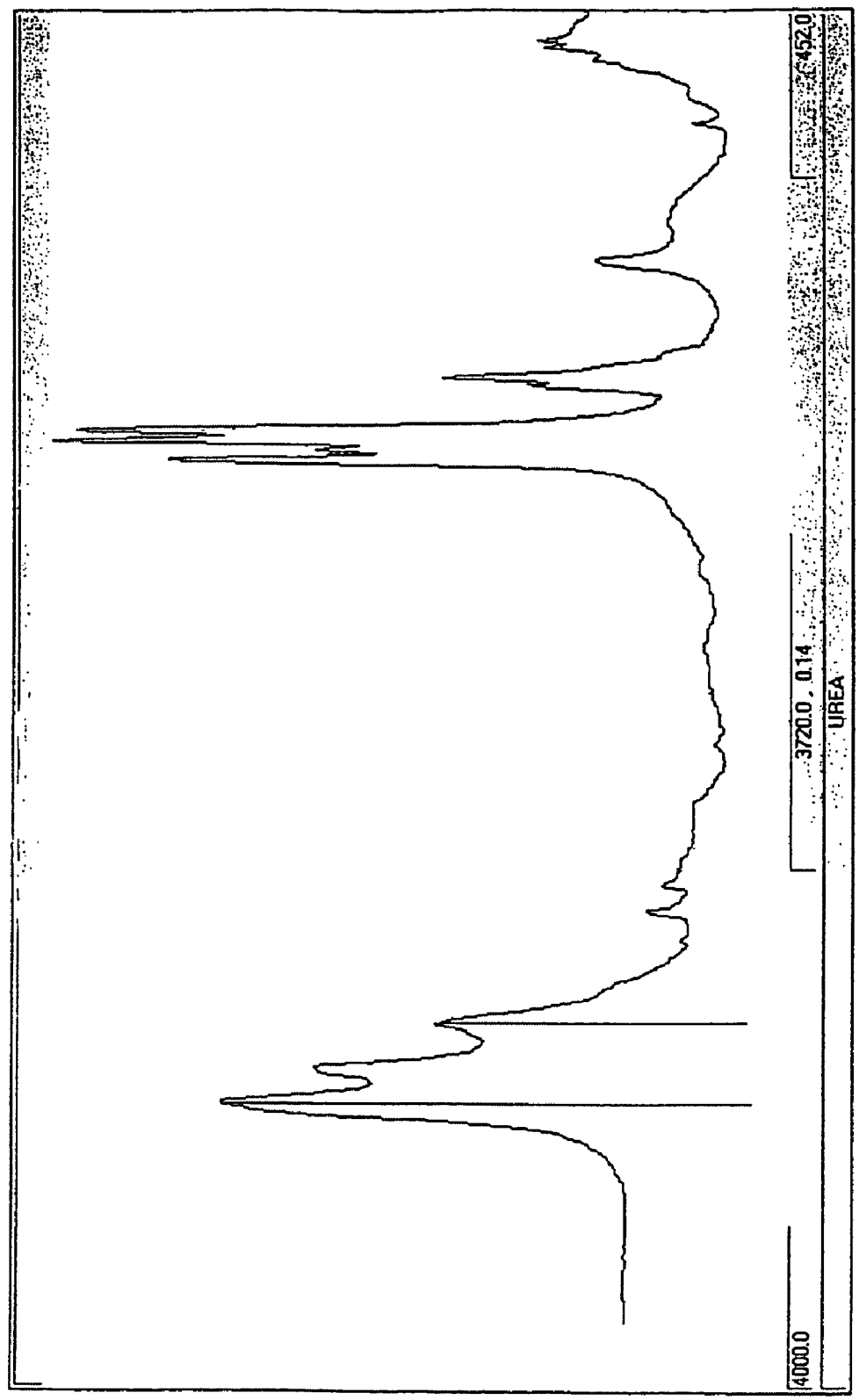
Figure 22A:
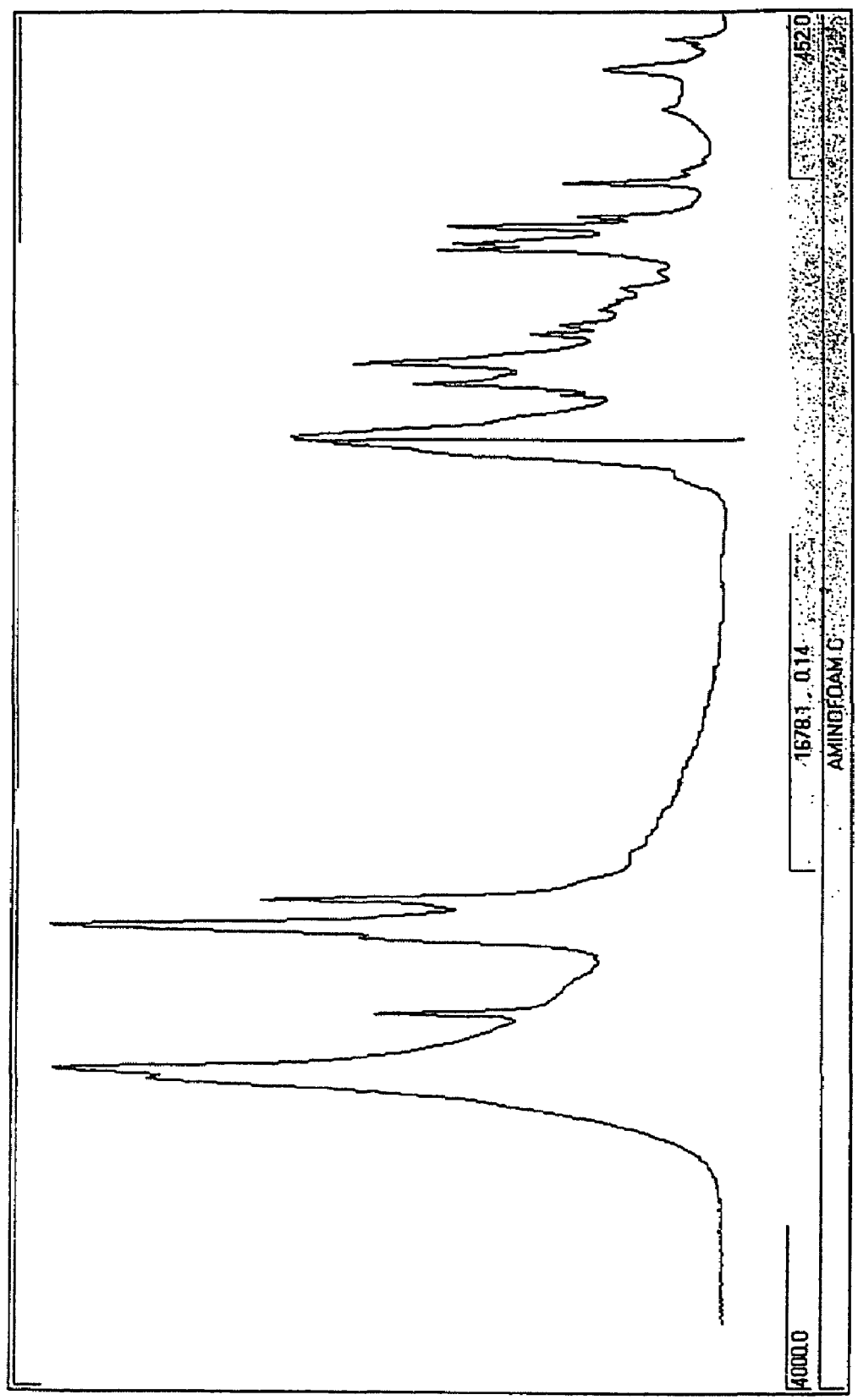
Figure 22O:
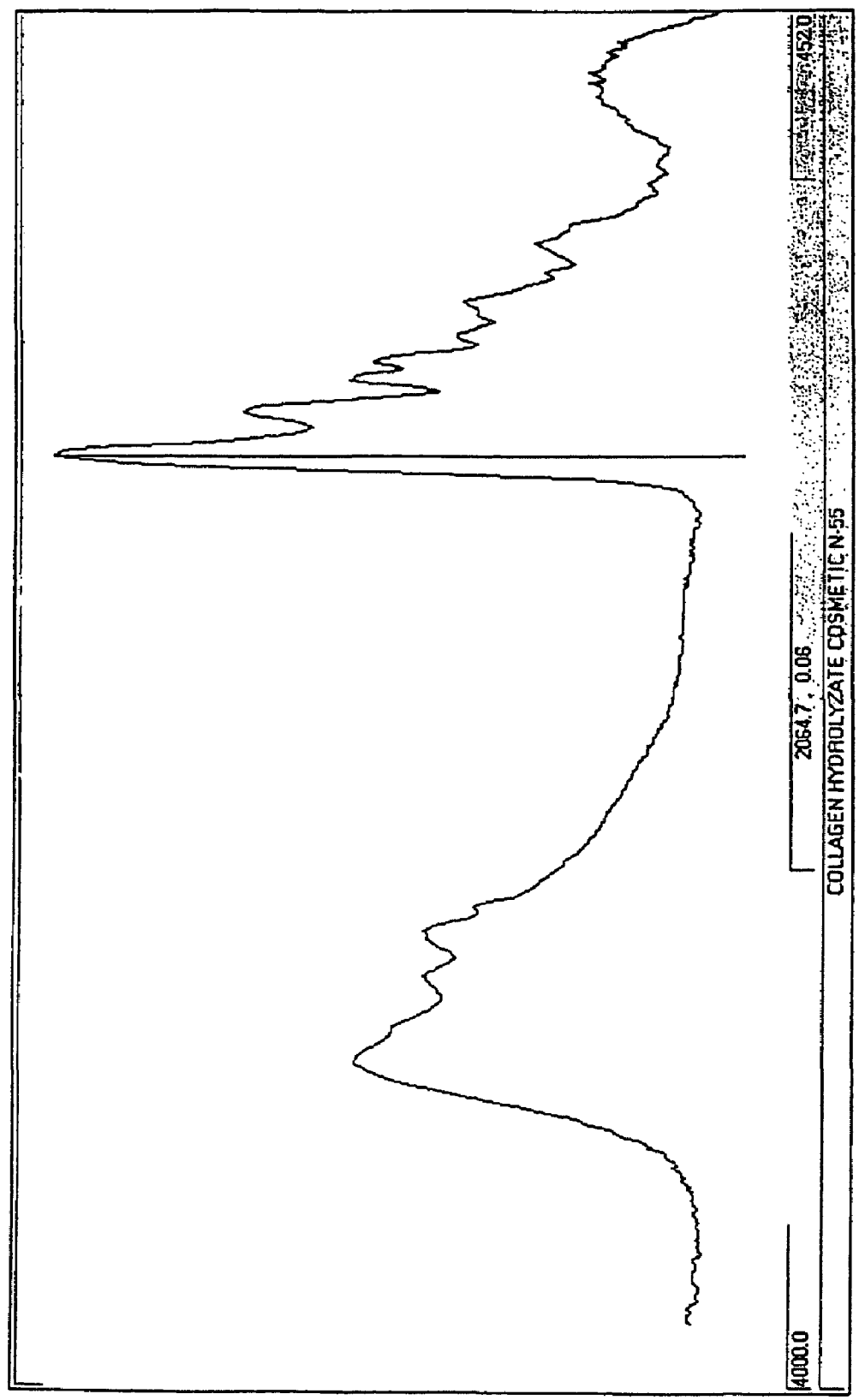
Figure 23A:
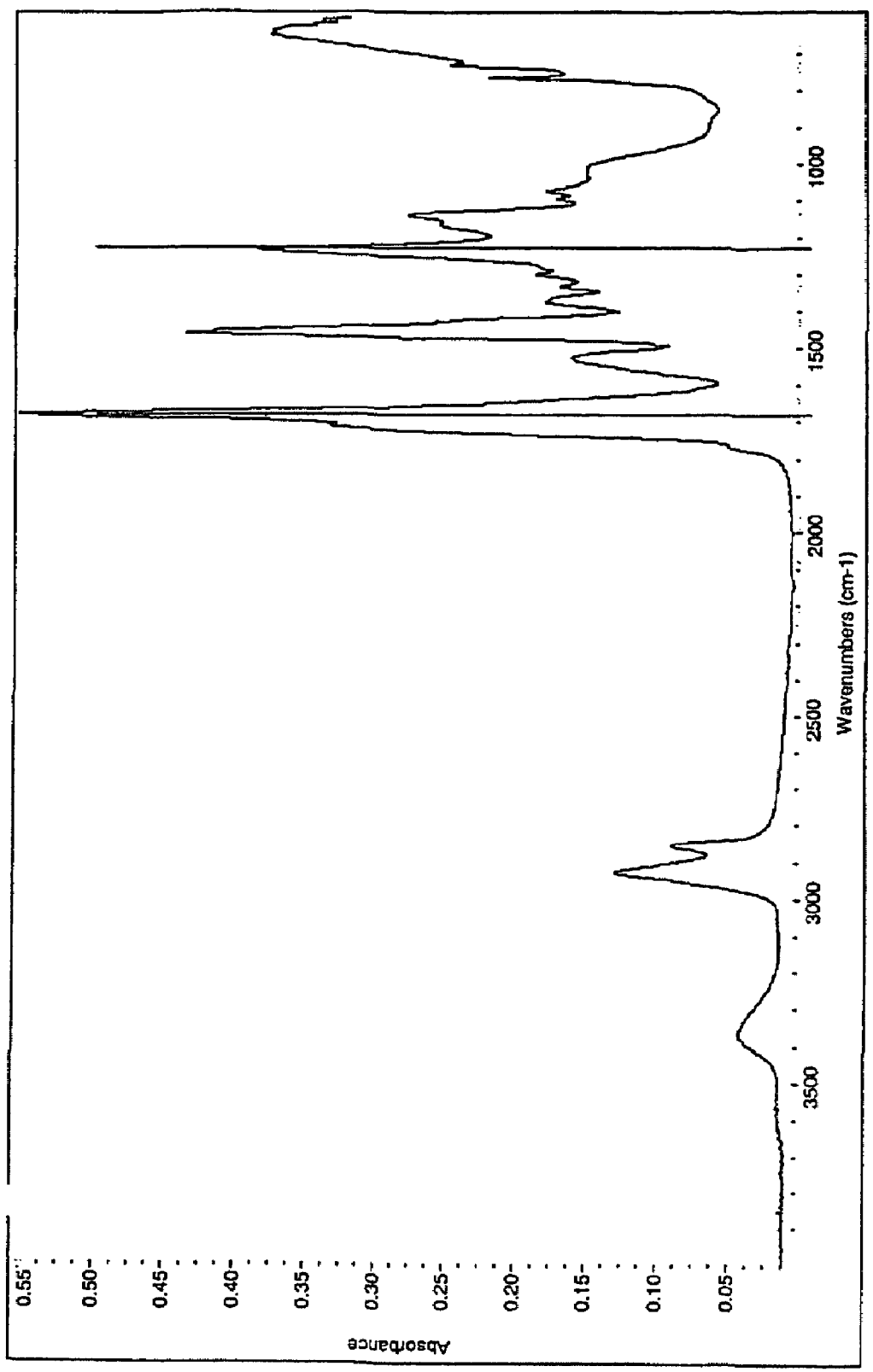
Figure 23C:
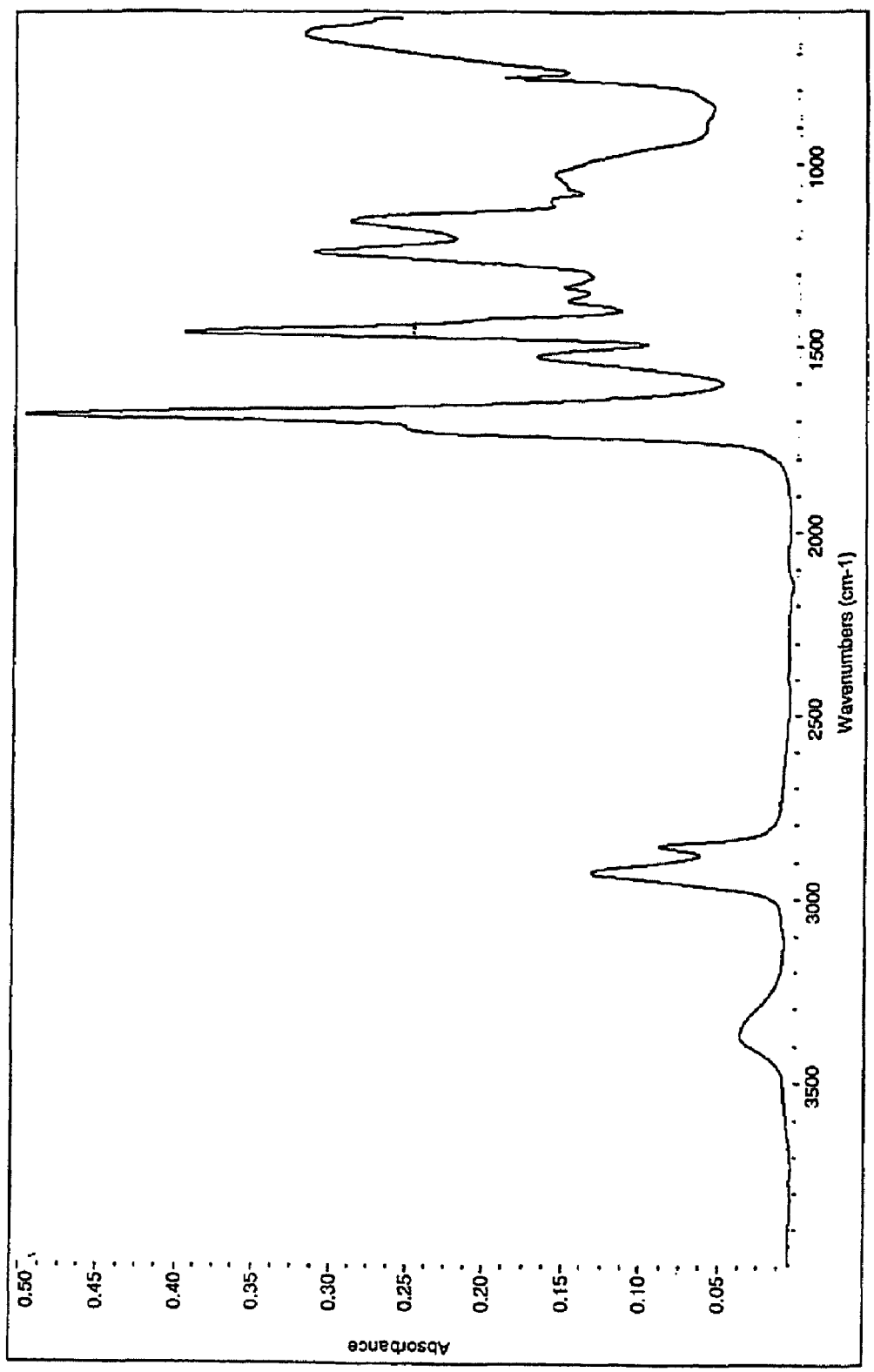
Figure 24A:
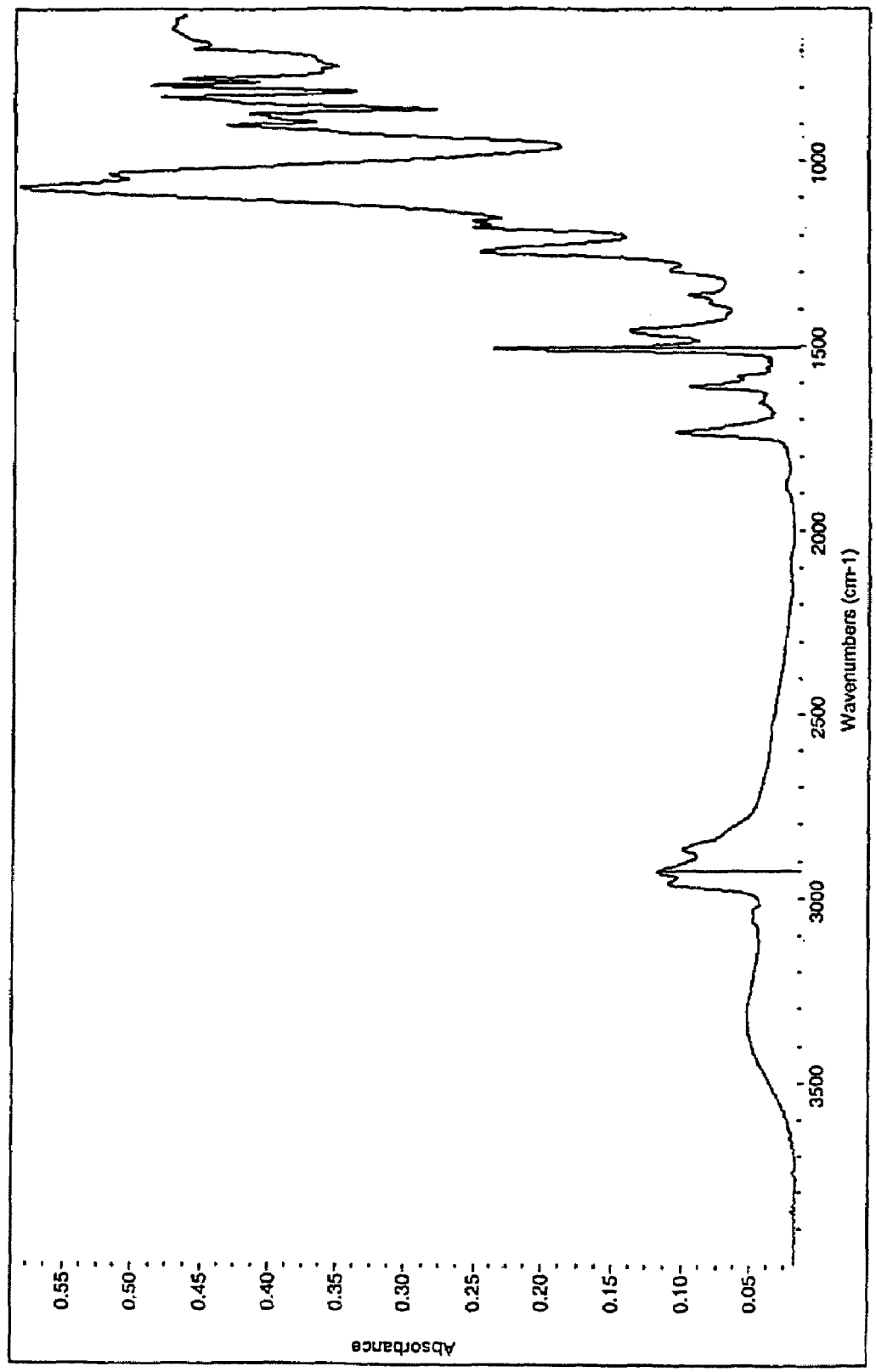
Figure 24B:
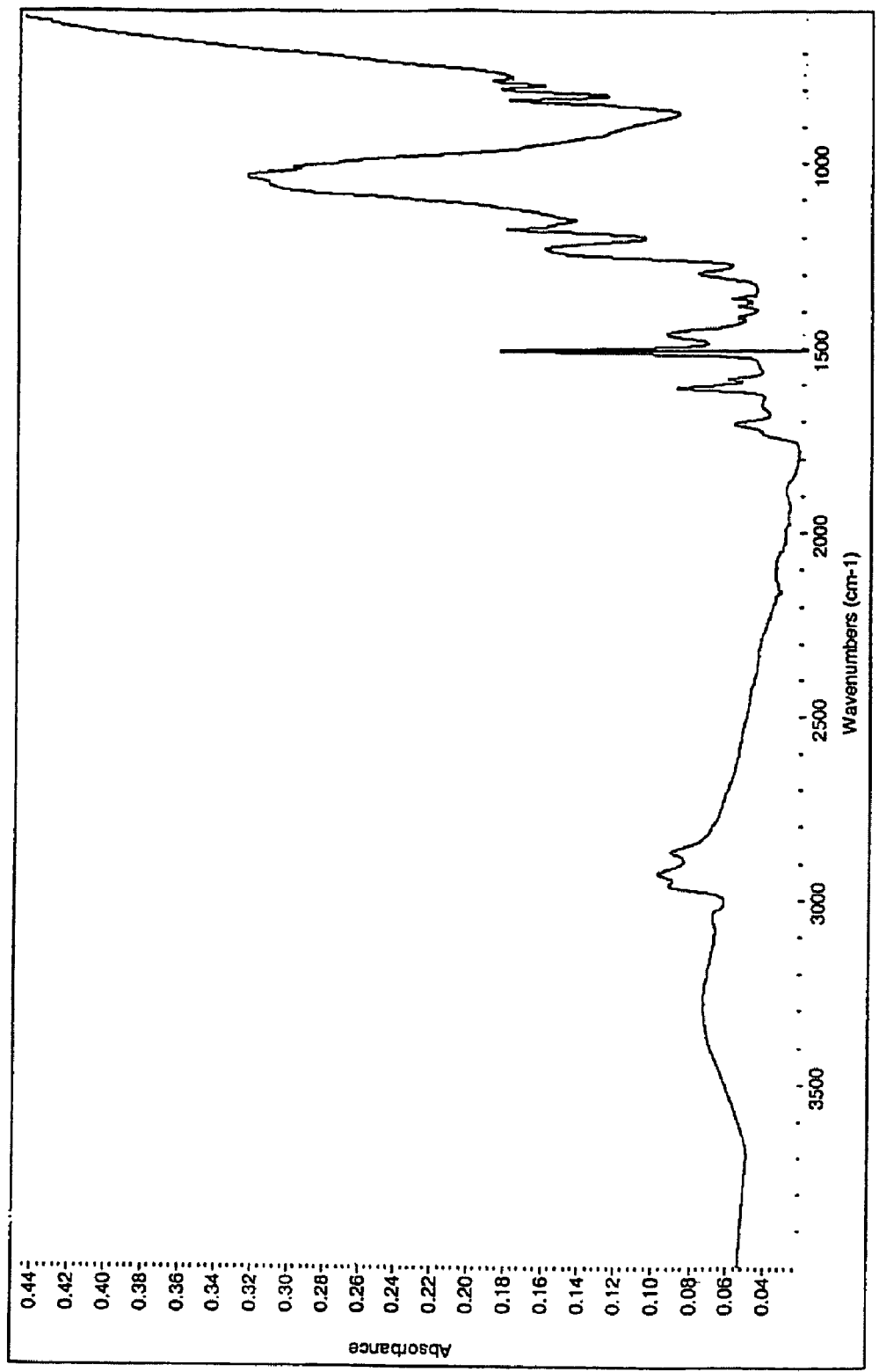
Figure 25:
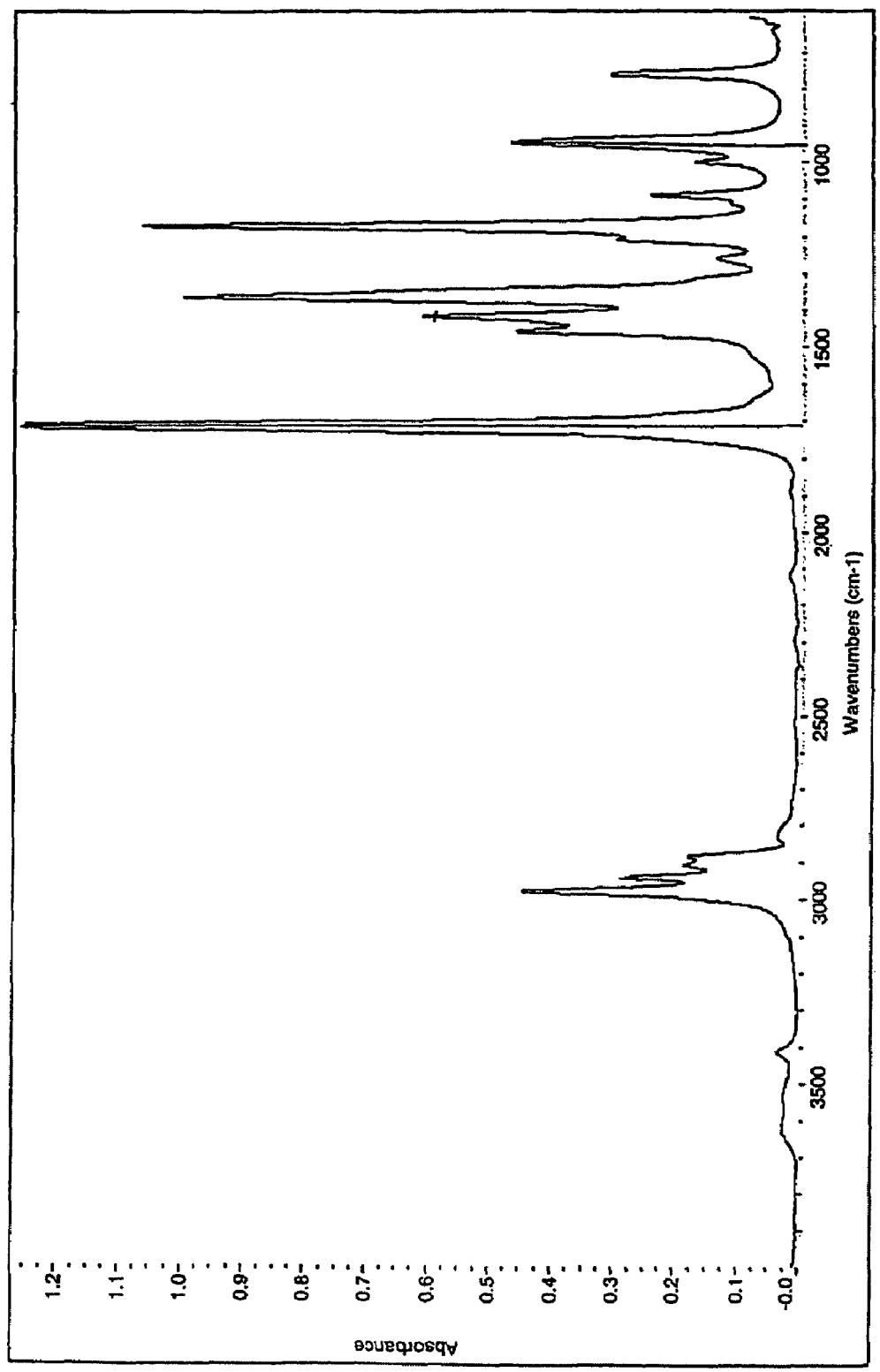

FIG. 18 is a graph of infrared absorbance of an exemplary release agent TEFLON®;

FIG. 19 is a graph of infrared absorbance of an exemplary protein lanolin;

FIG. 20 is a graph of infrared absorbance of an exemplary protein fingerprints;

FIG. 21 is a graph of an infrared absorbance of an exemplary protein urea;

FIG. 22A is a graph of an infrared absorbance of an exemplary protein collagen amino foam C;

FIG. 22B is a graph of an infrared absorbance of an exemplary protein collagen ritacollagen BA-1;

FIG. 22C is a graph of an infrared absorbance of an exemplary protein collagen amino collagen;

FIG. 22D is a graph of an infrared absorbance of an exemplary protein collagen hydolyzate cosmetic N-55;

FIG. 23A is a graph of an infrared absorbance of an exemplary polyurethane paint BMS 10-72 (white 420);

FIG. 23B is a graph of an infrared absorbance of an exemplary polyurethane paint BMS 10-72 (white-ECLIPSE);

FIG. 23C is a graph of an infrared absorbance of an exemplary polyurethane paint BMS 10-72 (white-DESOTHANE®);

FIG. 23D is a graph of an infrared absorbance of an exemplary polyurethane paint BMS 10-72 (gray-P-1000);

FIG. 24A is a graph of an infrared absorbance for an exemplary epoxy primer BMS 10-72;

FIG. 24B is a graph of an infrared absorbance for an exemplary epoxy primer BMS 10-103;

FIG. 24C is a graph of an infrared absorbance for an exemplary epoxy primer BMS 10-20;

FIG. 25 is a graph of an infrared absorbance of an exemplary solvent methyl ethyl ketone; and FIG. 26 is a flow chart of an exemplary testing method of the present invention.

DETAILED DESCRIPTION OF THE INVENTION

By way of overview, a non-destructive method is provided for determining presence of or identifying a contaminant on a substrate. According to an aspect of the invention, an infrared beam is transmitted onto a sample. A first infrared absorbance of the sample is determined at a first wave number. A second infrared absorbance of the sample is determined at a second wave number. The first absorbance is correlated to a first absorbance peak of a contaminant. The presence of a predetermined level of the contaminant is confirmed by correlating the second infrared absorbance to a second absorbance peak of the contaminant.

Figure 1:
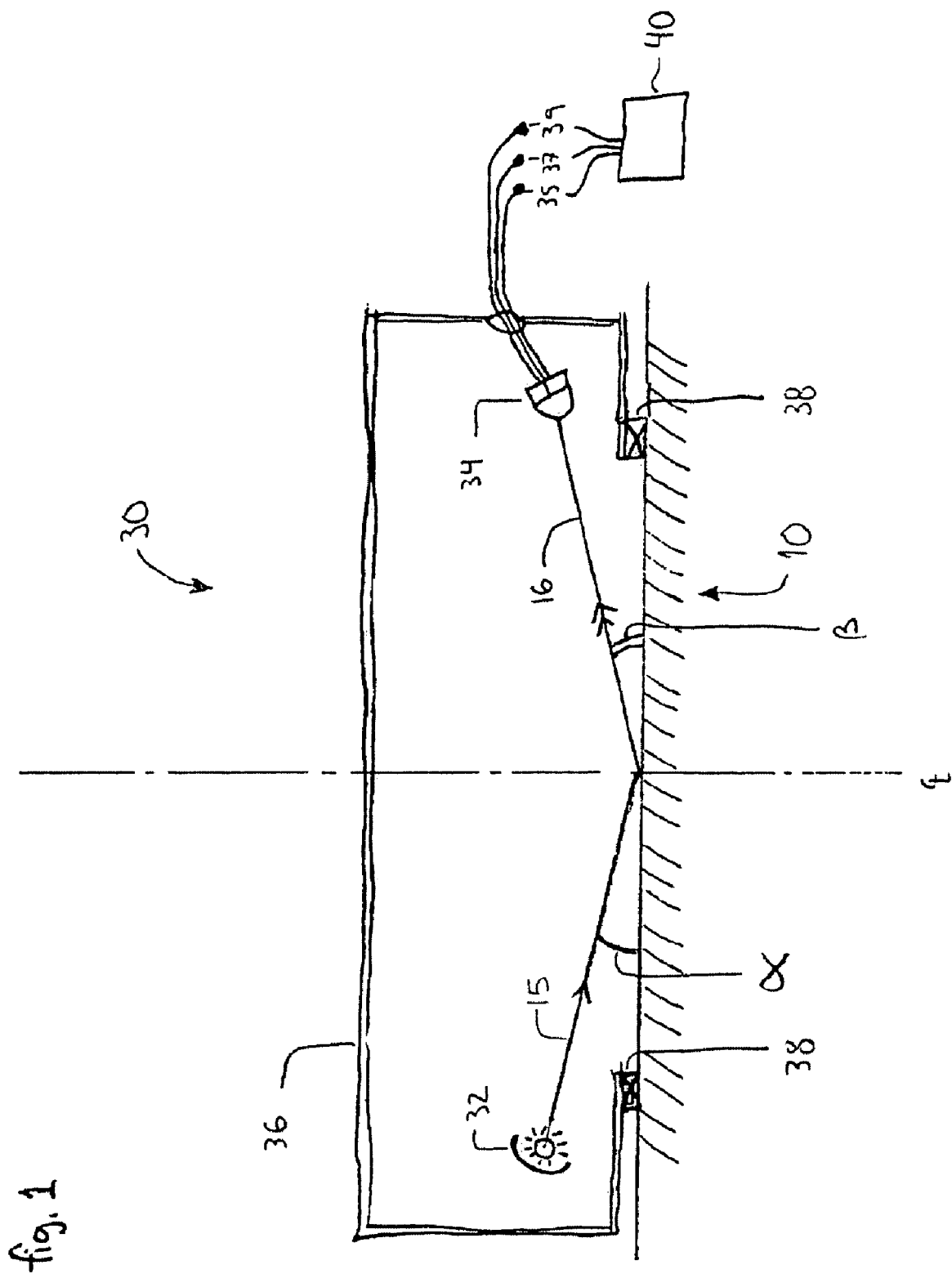
FIG. 1 is a cross-section of a contamination measurement device in accordance with an embodiment of the present invention.

Referring to FIG. 1, in one embodiment of the present invention, an exemplary testing device 30 is used to determine the presence of a predetermined level of a contaminant on a substrate or to identify a contaminant on the substrate. An infrared transmission beam 15 is transmitted by an infrared source 32. The beam 15 is reflected off the surface 10 and the reflected beam 16 is detected by an infrared detector 34. It will be appreciated that the infrared source 32 and the infrared detector 34 suitably may include an infrared spectrometer. The infrared source 32 suitably may include a multi-frequency infrared source, and the infrared detector 34 may include a single or multiple detector. In the embodiment shown in FIG. 1, the infrared detector 34 detects infrared energy at two wave numbers. The infrared levels received by the infrared detector 34 are output as an electrical signal to a processor or display 40 through a common conductor 37, a low frequency output conductor 35, and a high frequency output conductor 39. In one embodiment, the infrared source suitably is a broadband infrared source, and one or more narrow pass filters (not shown) are provided at the detector such that the reflected energy is detected at the two wavenumbers passed by the filters. In another presently preferred embodiment, the infrared source 32 and the infrared detector 34 are suitably included in a portable infrared spectrometer such as a SOC-400 FTIR manufactured by Surface Optics Corporation. In an alternative embodiment, an imaging infrared spectrometer may be utilized.

It will be appreciated that in one embodiment, the infrared beam 15 has an angle of incidence α to the surface 10 of approximately 15 degrees. The reflected infrared beam 15 has an angle of reflection β of 15 degrees from the surface 10. It will be appreciated that the angle of incidence a may vary, so long as consistent angles of incidence a and reflectance β are utilized for comparing results between different samples. Thus, the testing device 30 suitably measures a grazing infrared reflectivity of the surface 10. It will be appreciated that grazing reflection off the surface 10 in reflective materials, such as metals, is more sensitive to the presence of contaminants than acute reflection.

A housing 36 holds the infrared source 32 and infrared detector 34. The housing 36 rests on feet 38 that hold the infrared source 32 and infrared detector 34 at a predetermined distance and position relative to the surface 10. The mobility of the device permits additional sampling of adjoining areas and other samples with repeatable results. It will be appreciated that the testing device 30 shown in FIG. 1 suitably measures grazing angle specular reflectance at an angle greater than 70° from normal to the surface 10.

The device 30 of FIG. 1 may be utilized to non-destructively determine the presence of a predetermined amount of contamination or to identify a contamination on the surface 10 utilizing a method of the present invention. Initially, the infrared absorbance values of contaminated samples (not shown) are determined by measuring the infrared energy $I_r$ reflected from a reference contaminated surface. Absorbance $A_r$ of the reference contaminated surface is calculated as the $-\log 10$ of $(I_r/I_o)$ where $I_o$ is the value of infrared energy reflected by a base material, often gold, and $I_r$ is the value of infrared energy reflected by the sample under study. The device 30 is then used to transmit the infrared beam 15 to the surface 10 to be tested and a value $I_s$ of infrared energy reflected by the surface 10 is measured. Absorbance is derived as described above, and a comparison is made between the absorbance $A_s$ of the surface 10 and the absorbance $A_r$ of contaminated reference samples (not shown) at wave numbers correlated with particular contaminants being checked for. It will be appreciated that $I_s$ may be compared with $I_o$ without calculating absorbance. However, calculating and utilizing absorbance provides graphing and calculating convenience.

Figure 2:
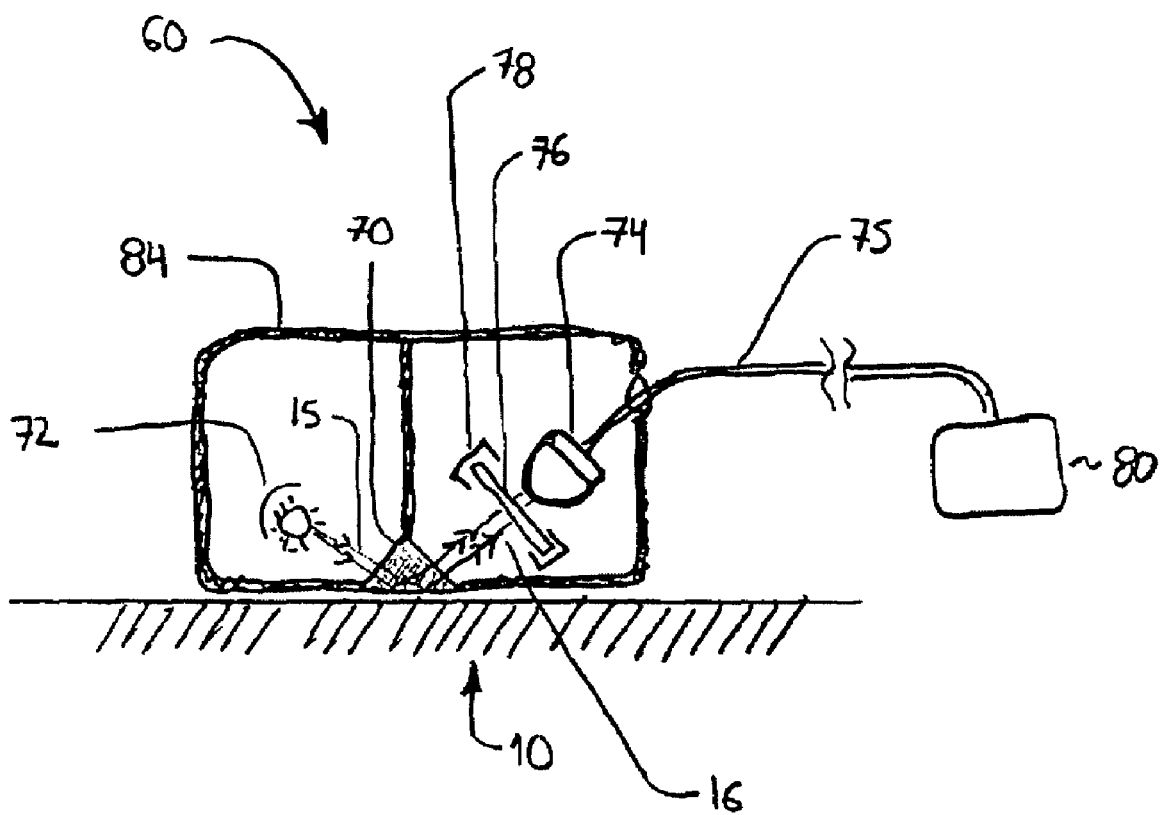
FIG. 2 is a cross-section of an exemplary contamination measurement device using attenuated total reflectance in accordance with another embodiment of the present invention.
Figure 3A:
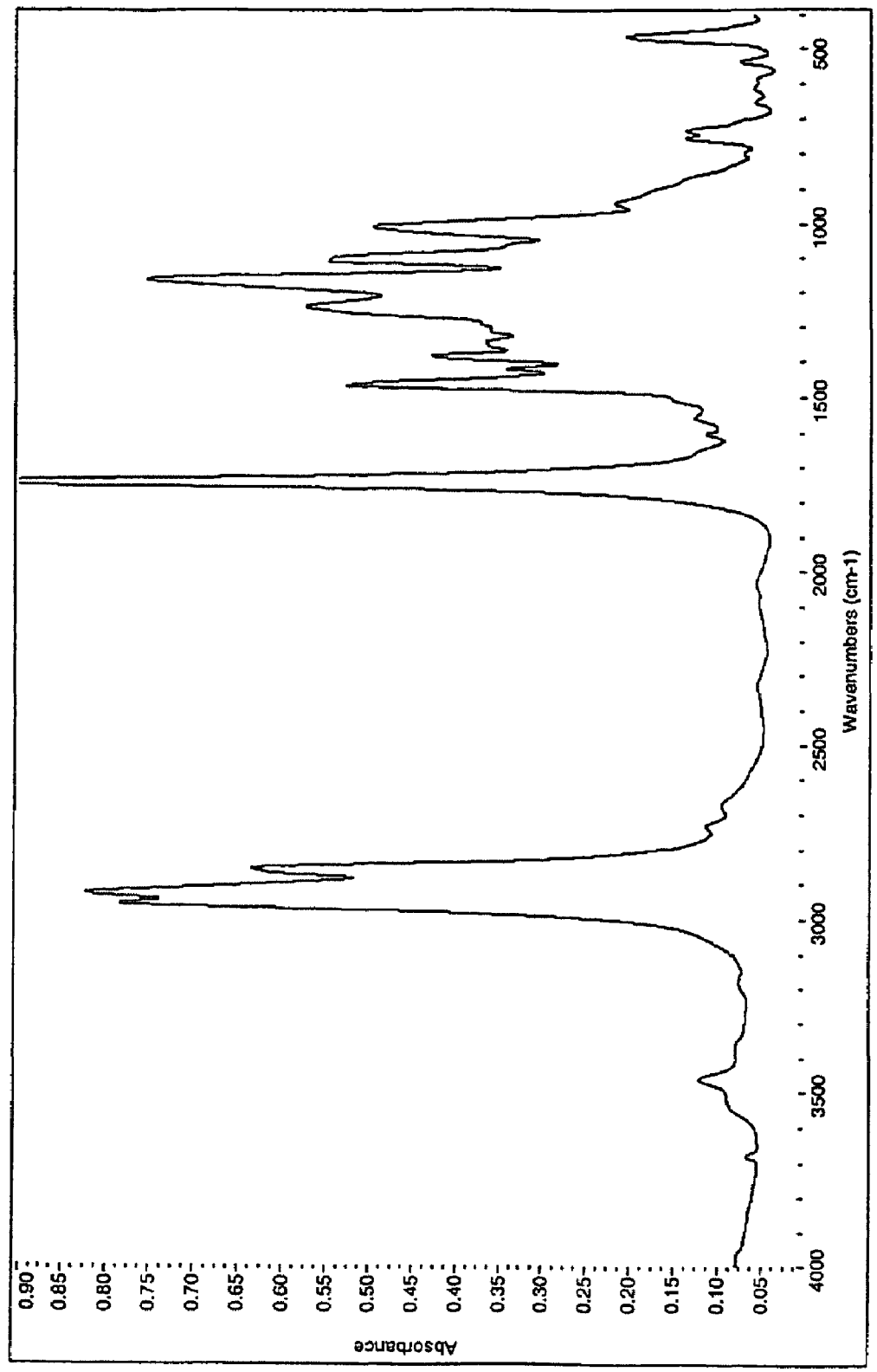
FIG. 3A is a graph of infrared absorbance of an exemplary grease BMS 3-24.
Figure 3B:
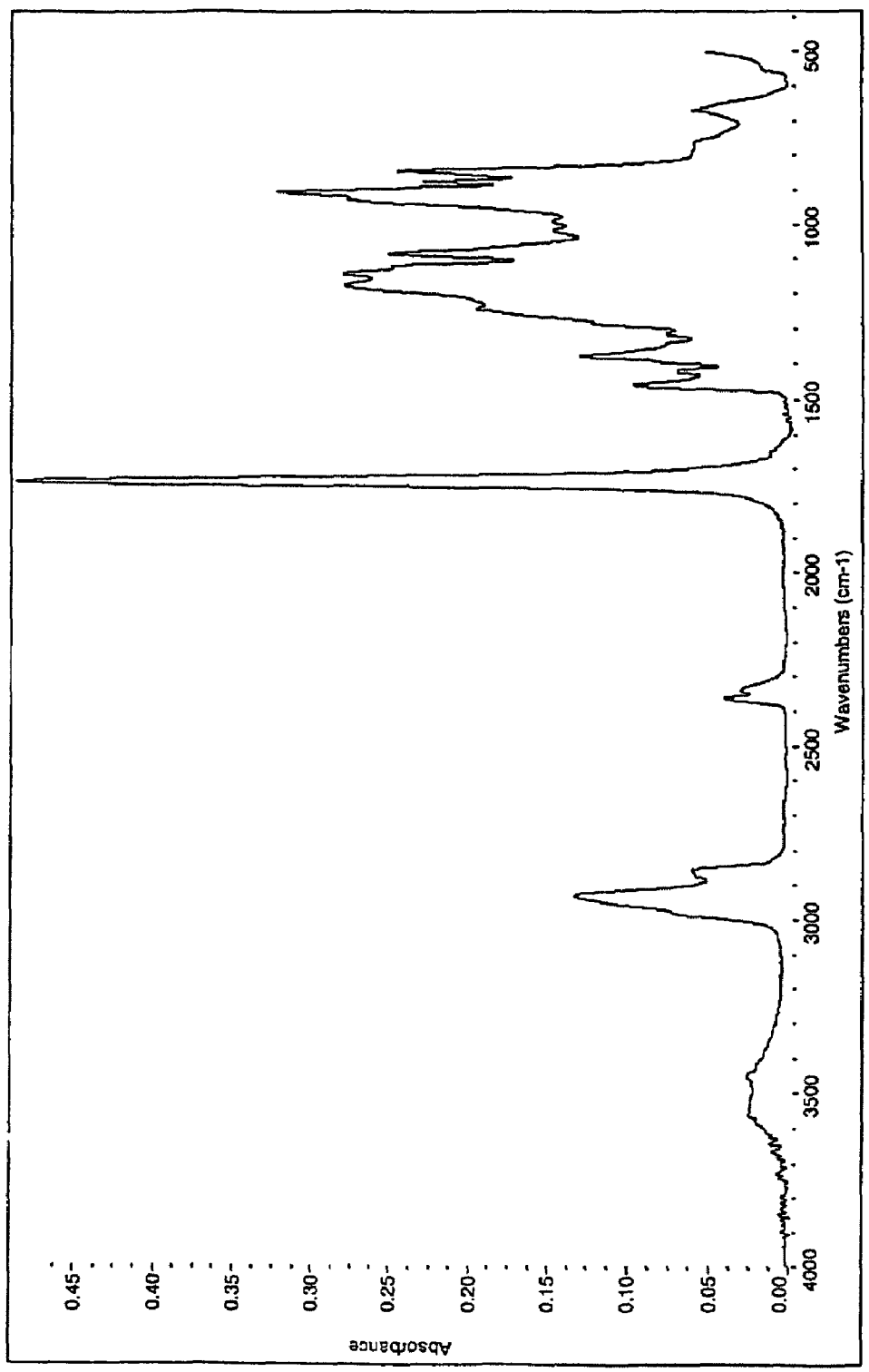
FIG. 3B is a graph of infrared absorbance of an exemplary grease BMS 3-27.
Figure 3C:
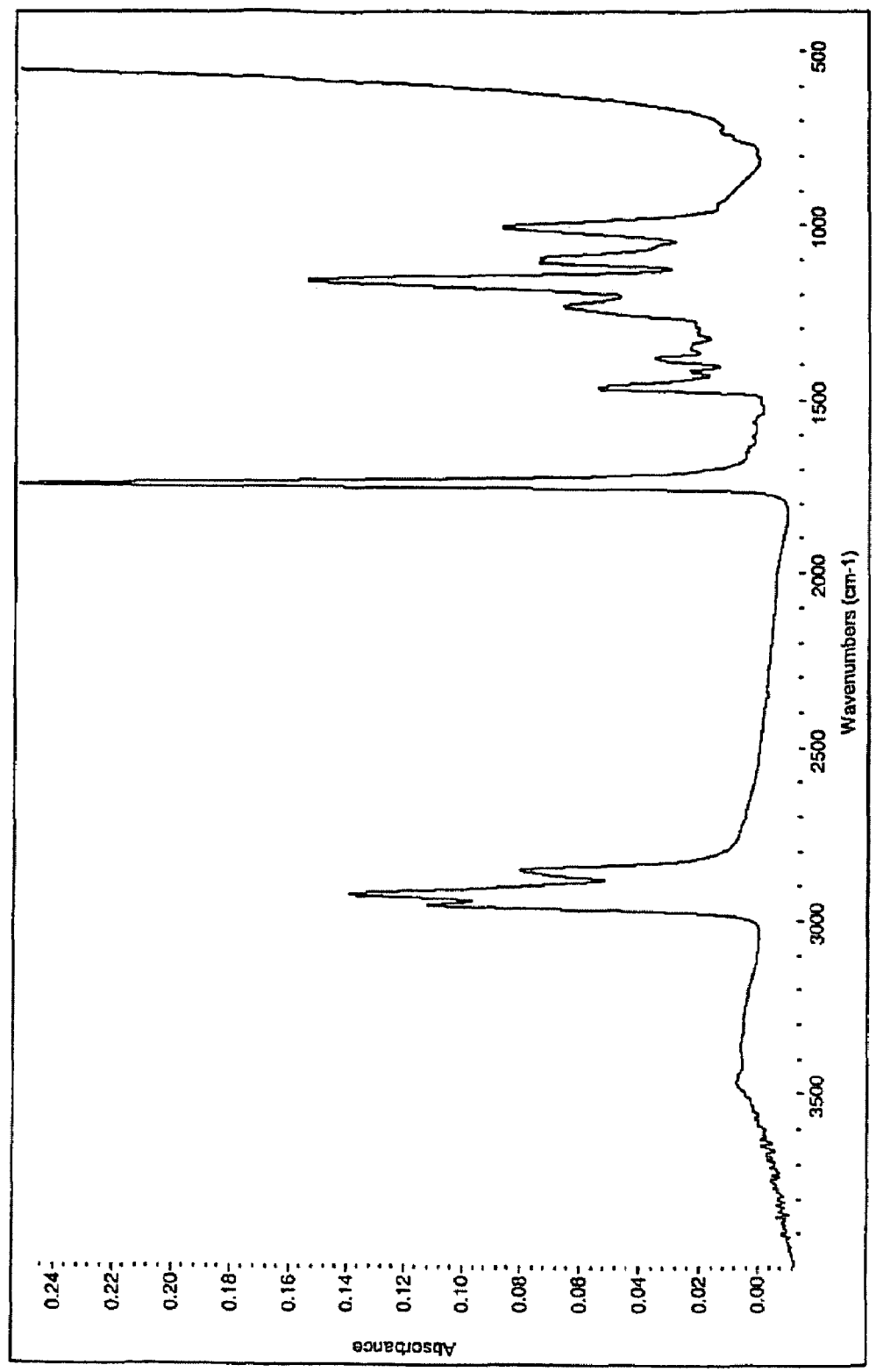
FIG. 3C is a graph of infrared absorbance of an exemplary grease BMS 3-33.
Figure 30:
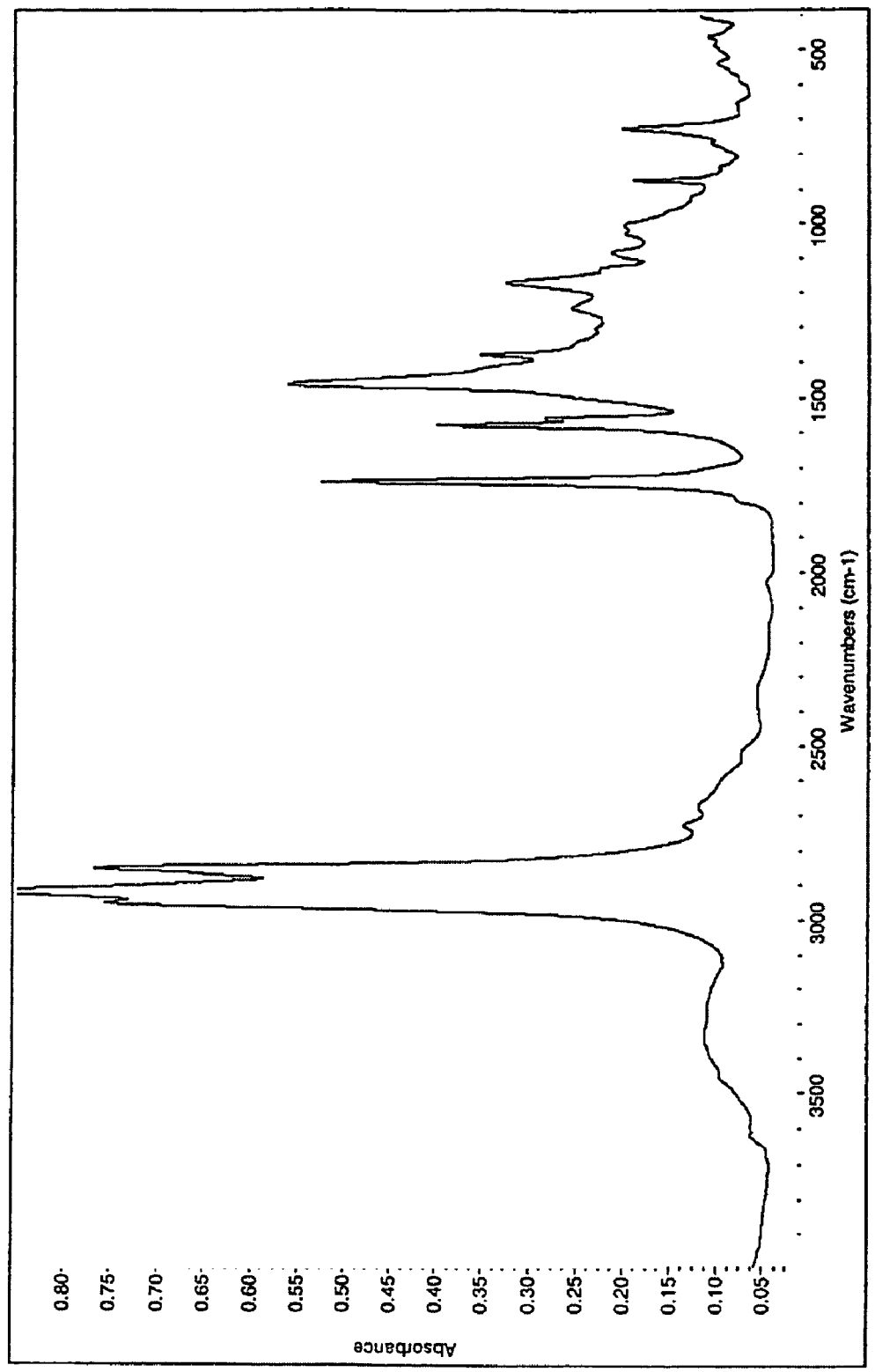

Referring now to FIG. 2, according to an alternate embodiment of the present invention an alternative exemplary testing device 60 may be utilized to determine the presence of a predetermined amount of contaminant or to identify a contaminant on a surface 10. The same reference numbers are used to refer to similar components of the device 10 (FIG. 1). An infrared beam 15 is transmitted by an infrared source 32. The beam 15 is transmitted through a crystal 70 placed against the surface 10. The crystal 70 suitably may include a diamond with a flat lower face for placing against surface. The beam 15 is reflected off the lower face of the crystal 70. Due to a wave interaction with the crystal 70 in contact with the surface 10, a portion of the infrared energy is absorbed. The reflected attenuated beam 16 is then detected by the infrared detector 74. As is known in the art, the use of the crystal 70 in this manner is referred to as Attenuated Total Reflectance (ATR). In this exemplary embodiment, the reflective beam 16 passes through a filter 76 removably held in a filter holder 78. An infrared detector 74 then detects the infrared energy of the reflected beam at a frequency passed by the filter 76. It will be appreciated that any number of suitable filters may be successfully placed in the filter holder 78, as desired, thereby permitting measurement of the Attenuated Total Reflectance of the surface 10 at a variety of wavelengths. Output from the infrared detector 74 is transmitted through a conductor 75 to a processor 84 for analysis or display. The infrared source 72, crystal 70, and detector 74 are suitably enclosed in a housing 84. The housing 84 may be successively placed against the surface 10, thereby permitting measurements to be taken at a variety of locations and surfaces. The device 60 may detect Attenuated Total Reflectance suitably utilizing one or more narrow pass filters 76 and a broadband infrared source 72. It will be appreciated that in alternative embodiments, by way of example but not limitation, an infrared spectrometer may be incorporated in the device 60 to permit measurement of Attenuated Total Reflectance of the surface 10 over a continuous frequency range.

Attenuated Total Reflectance infrared absorbance measurements suitably may be utilized on a variety of surfaces and substrates, but typically is utilized for non-reflective substrates. Such substrates include, by way of example but not limitation, epoxy fiber composites. Grazing angle reflectance, as described with reference to FIG. 1 above, is often utilized for reflective materials, such as metals. It will also be appreciated that acute angle reflectance, or diffuse infrared reflectance, may also be utilized for detecting and identifying contaminants according to the present invention, provided the infrared source and detector are of suitable sensitivity.

Reflectance at infrared wavelengths varies depending upon the contaminant on the substrate. First wavelengths for identifying the presence of contaminants and second wavelengths for confirming the presence of a contaminant or differentiating types of contaminants have been determined by testing for variety of materials related to manufacturing processes, including aircraft manufacturing. Use of the second wavelength advantageously permits confirmation of the presence of a contaminant.

Calibration or determining absorbances at the first wavelength and the second wavelengths indicating the presence of a predetermined level of a contaminant on a substrate, by way of example but not limitation, suitably may be accomplished by applying the contaminant to the substrate in known quantities and recording absorbances at the first and second wavelengths. Predetermined levels or quantities of contaminants on the substrate suitably may be measured by weight per area, such as mg/square foot. Absorbances at the first and second wavelengths greater than the recorded absorbances have been found to indicate greater than the measured predetermined level of the contaminant on the substrate.

Turning to FIGS. 3A through 3D, absorbance of exemplary grease contaminants is graphed at infrared wavenumbers between approximately 400 to approximately 4,000, with absorbance graphed vertically. As is known, wavenumbers are the numbers of wavelengths per centimeter within the infrared spectrum. It can be a graphing convenience to present infrared absorbance by wavenumbers (cm−1), as opposed to wavelength in microns (μ). FIGS. 3A through FIGS. 3D show the absorbance spectrum for three Boeing Material Services ("BMS" herein) greases, 3-24, 3-27, 3-33, and 3-34, respectively. It will be appreciated that these greases show a first absorbance peak at approximately 2,924 to 2,933 cm−1, and a second absorbance peak at approximately 1,739 cm−1. Measurement of absorbance at these two wavenumbers has been determined to differentiate these greases from other lubricants and other common manufacturing compounds, such as those described below.

Figure 4:
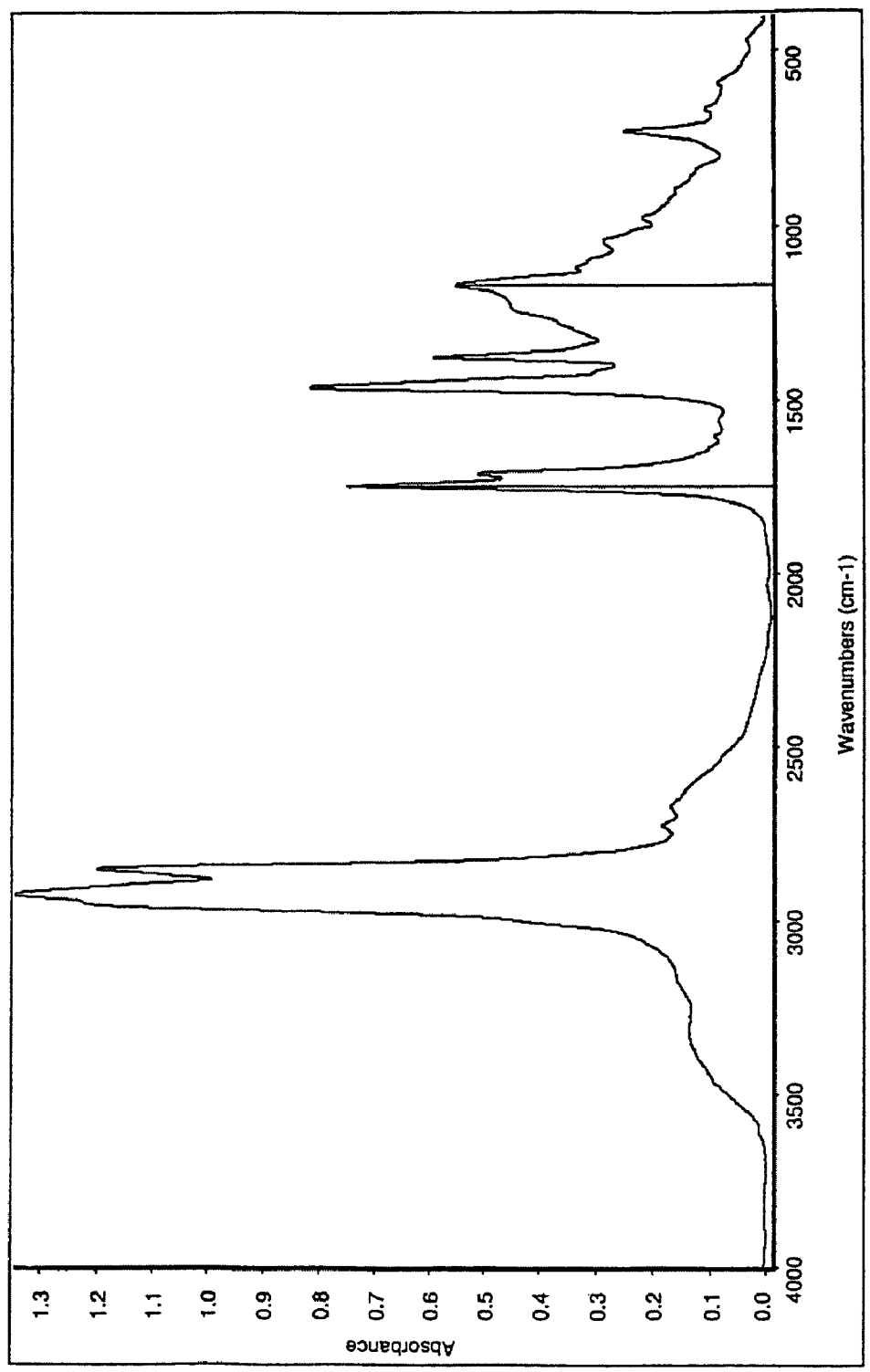
FIG. 4 is graph of infrared absorbance of an exemplary lubricant, MICROCUT®, that is similar to a synthetic oil, as described in Boeing Material Safety Data Sheet (MSDS) No. 55492, revised Apr. 25, 1989, the content of which is hereby incorporated by reference. MICROCUT® has a first identifiable absorbance peak at 1745 cm−1 and a second identifiable absorbance peak at 1170 cm−1 that have been found to differentiate MICROCUT® from other contaminants.

FIG. 4 is graph of infrared absorbance of an exemplary lubricant, MICROCUT®, that is similar to a synthetic oil. MICROCUT® has a first identifiable absorbance peak at 1745 cm−1 and a second identifiable absorbance peak at 1170 cm−1 that have been found to differentiate MICROCUT® from other contaminants.

Figure 5:
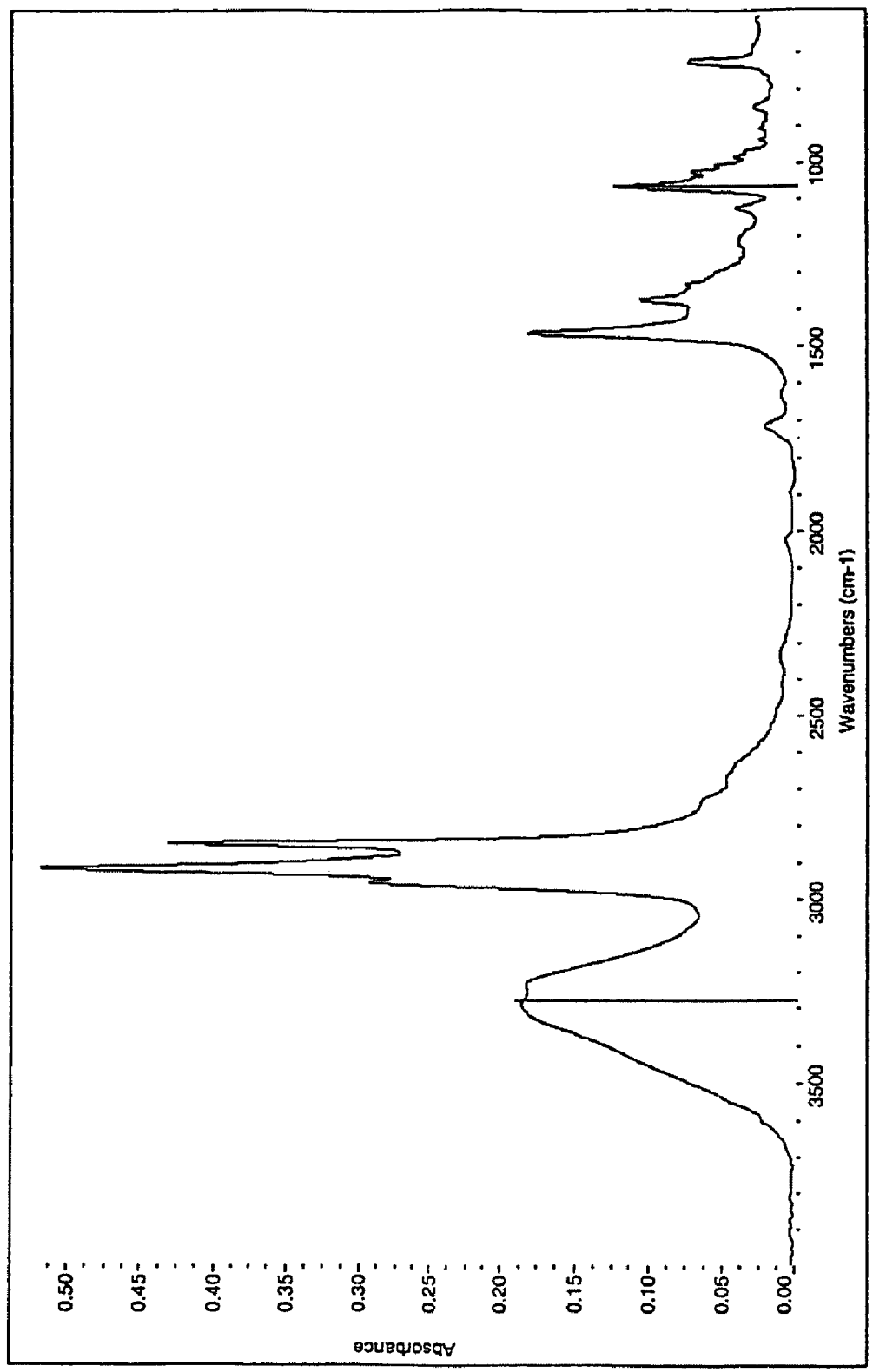
FIG. 5 is a graph of infrared absorbance of an exemplary general lubricant, BOELUBE®, a general lubricant, as described in the Orelube Corporation Material Safety Data Sheet (MSDS) prepared Mar. 20, 2003, the content of which is hereby incorporated by reference.

FIG. 5 is a graph of infrared absorbance of an exemplary general lubricant, BOELUBE®, a general lubricant. As shown in FIG. 5, this lubricant has identifiable absorbance peaks at 1071 cm−1, and at 3279 cm−1, that suitably differentiate this lubricant from other common manufacturing contaminants.

Corrosion inhibiting compounds may also be detected and identified utilizing the method of the present invention. FIG. 6 is a graph of infrared absorbance of an exemplary corrosion inhibiting compound, DINITROL® AV30, manufactured by Dinol International. DINITROL® AV30 has identifiable absorbance peaks at 2,924 cm−1 and at 1,060 cm−1.

FIG. 7 is a graph of infrared absorbance of an exemplary corrosion inhibiting compound, DINITROL® AV8, manufactured by Dinol International. DINITROL® AV8 has identifiable absorbance peaks at 2,924 cm−1 and at 752 cm−1.

FIG. 8 is a graph of infrared absorbance of an exemplary corrosion inhibiting compound, BRAYCOTE® 248, manufactured by Castrol, Inc. BRAYCOTE® 248 has identifiable absorbance peaks at 2,924 cm−1 and at 1,460 cm−1.

FIG. 9 is a graph of infrared absorbance of an exemplary corrosion inhibiting compound, CORBAN™, manufactured by Zip Chem Products. CORBAN™ has identifiable absorbance peaks at 2,924 cm−1 and at 752 cm−1.

FIG. 10 is a graph of infrared absorbance of exemplary chromate conversion coating Converted ALODINE® 1200, manufactured by Henkel Surface Technologies. ALODINE® 1200 has identifiable absorbance peaks at 925 cm−1 and 2,190 cm−1.

Cleaners and soaps also may be identified as a contaminant using a method of the present invention.

FIG. 11 is a graph of infrared absorbance of an exemplary cleaner/soap, ALKASOL 27. ALKASOL 27 has identifiable absorbance peaks at 1,060 cm−1 and at 1,600 cm−1.

FIG. 12 is a graph of infrared absorbance of an exemplary cleaner/soap, JET CLEAN E manufactured by Melrose Chemicals Limited. JET CLEAN E has identifiable absorbance peaks at 1,241 cm−1 and at 2,551 cm−1.

FIG. 13 is a graph of infrared absorbance of an exemplary cleaner/soap, PACE B82. PACE B82 has identifiable absorbance peak at 1120 cm−1 and at 901 cm−1.

FIG. 14 is a graph of infrared absorbance of an exemplary cleaner/soap, SNOOP. SNOOP has identifiable absorbance peaks at 1,180 cm−1 and at 1,620 cm−1.

FIG. 15 is a graph of infrared absorbance of an exemplary temporary protective coating used in manufacturing, SPRAYLAT manufactured by Spraylat Corporation. SPRAYLAT has been found to have identifiable absorbance peaks at 1730 cm−1 and 3300 cm−1 to differentiate from other common manufacturing contaminants.

FIG. 16 is a graph of infrared absorbance of an exemplary temporary protective coating used in manufacturing, AZTEC. AZTEC has been found to have identifiable absorbance peaks at 1730 cm−1 and 1160 cm−1 to differentiate from other common manufacturing contaminants.

FIG. 17 is a graph of infrared absorbance of an exemplary form release agent, a silicone oil FREKOTE®, manufactured by Loctite Corporation. Release agents are used when forming plastics or epoxy fiber composites to prevent the material from sticking to a form. Silicone oil has been found to have identifiable absorbance peaks at 1259 cm−1 and 800 cm−1.

FIG. 18 is a graph of infrared absorbance of an alternate exemplary form release agent, TEFLON®. TEFLON® has been found to have identifiable absorbance peaks at 1212 cm−1 and 1155 cm−1.

Manufacturing materials may also be contaminated by a variety of natural products from humans or animals.

FIG. 19 is a graph of absorbance for an exemplary natural product lanolin, in this example, cosmetic grade lanolin. Lanolin has been found to have identifiable absorbance peaks of 1745 cm−1 and 1180 cm−1.

FIG. 20 is a graph of absorbance for an exemplary natural product fingerprints. Fingerprints have been found to have identifiable absorbance peaks of 2924 cm−1 and 1751 cm−1.

FIG. 21 is a graph of absorbance for an exemplary natural product urea. Urea has been found to have identifiable absorbance peaks of 3425 cm−1 and 3195 cm−1.

FIGS. 22A through D are graphs of infrared absorbance for collagen proteins, aminofoam C, ritacollagen BA-1, aminocollagen, and collagen hydrolyzate cosmetic N-55, (hydrolyzed collagen) respectively. Collagen proteins are often used in cosmetics. It has been found that collagens have identifiable absorbance peaks at 1650 cm−1 and 3300 cm−1.

FIGS. 23A through D are graphs of infrared absorbance of exemplary polyurethane paints, BMS 10-72 (white 420), BMS 10-72 (white-eclipse), BMS 10-72 (white-DESOTHANE®), and MBS 10-72 (gray-P1000), respectively. From these graphs, absorbance peaks at 1681 cm−1 and 1230 cm−1 have been found to identify and differentiate polyurethane paint as a contaminant from other manufacturing contaminants.

FIGS. 24A through C are graphs of infrared absorbance of an exemplary epoxy primer, BMS 10-72, BMS 10-103, and BMS 10-20, respectively. Epoxy primers suitably exhibit absorbance peaks at 1502 cm−1 and 2924 cm−1 that indicate their presence and differentiate them from other common manufacturing contaminants.

Solvent residues may also affect subsequent coating applications on materials.

FIG. 25 is a graph of infrared absorbance of exemplary solvent methyl ethyl ketone (MEK). MEK suitably has absorbance peaks at 1709 cm−1 and 960 cm−1 that indicate its presence and differentiate it from other common manufacturing contaminants.

The absorbance peaks for the substances described with respect to FIGS. 3 through 25 are compiled into TABLE 1:

TABLE 1

| Type of Contaminant | Contaminant | First wavelength in microns | Absorbance Peak 1 (cm−1) | Second wavelength in microns | Absorbance Peak 2 (cm−1) |
| --- | --- | --- | --- | --- | --- |
| Hydrocarbon oil | BMS 3-24 | 3.42 | 2924 | 5.75 | 1739 |
| Hydrocarbon oil | BMS 3-27 | 3.41 | 2933 | 5.75 | 1739 |
| Hydrocarbon oil | BMS 3-33 | 3.42 | 2924 | 5.75 | 1739 |
| Hydrocarbon oil | BMS 3-34 | 3.41 | 2933 | 5.75 | 1739 |
| Lubricants | BOELUBE ® | 9.34 | 1071 | 3.05 | 3279 |
| Lubricants | MICROCUT ® | 5.73 | 1745 | 8.55 | 1170 |
| Corrosion inhibiting compounds (CIC) | DINITROL ® AV8 | 3.42 | 2924 | 9.43 | 1060 |
| Corrosion inhibiting compounds (CIC) | DINITROL ® AV30 | 3.42 | 2924 | 13.3 | 752 |
| Corrosion inhibiting compounds (CIC) | BRAYCOTE ® 248 | 3.42 | 2924 | 6.85 | 1460 |
| Corrosion inhibiting compounds (CIC) | CORBAN ™ | 3.42 | 2924 | 13.3 | 752 |

TABLE 1-continued

| Type of Contaminant | Contaminant | First wavelength in microns | Absorbance Peak 1 (cm−1) | Second wavelength in microns | Absorbance Peak 2 (cm−1) |
|---|---|---|---|---|---|
| Anodizating byproduct | ALODINE ® 1200 | 10.81? | 925? | 4.55? | 2190? |
| Cleaners/soaps | ALKASOL 27 | 9.43 | 1060 | 6.25 | 1600 |
| Cleaners/soaps | JET CLEAN E | 8.06 | 1241 | 3.92 | 2551 |
| Cleaners/soaps | PACE B82 | 8.93 | 1120 | 11.1 | 901 |
| Cleaners/soaps | SNOOP | 8.47? | 1180? | 6.17? | 1620? |
| Temporary protective coatings (TPC) | SPRAYLAT | 5.78 | 1730 | 3.03 | 3300 |
| Temporary protective coatings (TPC) | AZTEC | 5.78 | 1730 | 8.62 | 1160 |
| Release agents | FREKOTE ® (silicone) | 7.94 | 1259 | 12.5 | 800 |
| Release agents | TEFLON ® | 8.25 | 1212 | 8.66 | 1155 |
| Natural products | Lanolin | 5.73 | 1745 | 8.47 | 1180 |
| Natural products | Finger prints | 3.42 | 2924 | 5.71 | 1751 |
| Natural products | Urea | 2.92 | 3425 | 3.13 | 3195 |
| Natural products | Collagen (protein) | 6.06 | 1650 | 3.03 | 3300 |
| Aircraft paint | Polyurethane | 5.95 | 1681 | 8.13 | 1230 |
| Aircraft paint | Epoxy primer | 6.66 | 1502 | 3.42 | 2924 |
| Solvent residue | MPK/MEK residue | 5.85 | 1709 | 10.42 | 960 |

FIG. 26 is a flow chart of an exemplary testing method 300 of the present invention. At a block 305, absorbance at a first wavenumber utilizing a first filter 1 is completed, thereby testing for a suspected contaminant. A determination is made as to whether a contaminant is present at a decision block 310 by determining whether an absorbance peak or absorbance level over a predetermined amount is present at the tested for wavenumber. If a contaminant presence is not indicated at the block 310 a determination is made at a block 330 as to whether further testing is desired. If further testing is desired, the method returns to the block 305 for checking for another contaminant at an alternate wavenumber. If further testing is not required, the substrate is determined to pass at an output block 340.

At the decision block 310 if an absorbance or absorbance peak is determined at the wavenumber sampled, then the sample is measured at a second wavenumber to determine a second absorbance $A_2$. In this example a second filter is utilized in at a block 315. At a decision block 320 an evaluation is determined as to whether or not the absorbance $A_2$ confirms the contaminant. If the contaminant is confirmed by high absorbance or an absorbance peak $A_2$ at the second measured wavenumber, the material fails or the presence of contamination is confirmed. The failure results indicating a contaminant are output at an output block 325. If the evaluation at the decision block 320 to confirm the contaminant does not result in confirmation of the presence of a contaminant, the process moves to the decision block 330 where an inquiry is made as to whether further testing is desired. At the decision block 330, if further testing is desired the method returns to the block 305 described above. If further testing is not desired the material passes as not having the presence of contaminant or without a contaminant identified at the output block 340.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A non-destructive method for identifying a contaminant on a substrate, the method comprising:
    exposing the substrate to a multi-frequency infrared energy source;
    determining at least two infrared energy absorbance peaks, the first absorbance peak at a first wavenumber, and the second absorbance peak at a second wavenumber; and
    identifying the contaminant on the surface by correlating the at least two absorbance peaks to the known absorbance peaks of a contaminant at the first and second wavenumbers.

2. The method of claim 1, wherein determining the at least two absorbance peaks includes utilizing an infrared spectrometer.

3. The method of claim 2, wherein the infrared spectrometer includes an infrared filter spectrometer.

4. The method of claim 2, wherein the infrared spectrometer includes an ellipsoidal mirror collector.

5. The method of claim 2, wherein the infrared spectrometer includes an attenuated total reflectance collector.

6. The method of claim 2, wherein the infrared spectrometer includes at least two filters.

7. The method of claim 6, wherein the at least two filters include narrow bandpass infrared filters.

8. The method of claim 1, wherein the at least two wavenumbers are around 2924 cm−1 and around 1739 cm−1.

9. The method of claim 1, wherein the at least two wavenumbers are around 2933 cm−1 and around 1739 cm−1.

10. The method of claim 1, where in the contaminant includes grease.

11. The method of claim 1, wherein the at least two wavenumbers are around 1071 cm−1 and around 3279 cm−1.

12. The method of claim 1, wherein the contaminant includes BOELUBE®.

13. The method of claim 1, wherein the at least two wavenumbers are around 1745 cm−1 and around 1170 cm−1.

14. The method of claim 1, wherein the contaminant includes MICROCUT®.

15. The method of claim 1, wherein the at least two wavenumbers are around 2924 cm−1 and around 1060 cm−1.

16. The method of claim 1, wherein the contaminant includes DiNITROL® AV8.

17. The method of claim 1, wherein the at least two wavenumbers are around 2924 cm−1 and around 752 cm−1.

18. The method of claim 1, wherein the contaminant includes DINITROL® AV30.

19. The method of claim 1, wherein the at least two wavenumbers are around 2924 cm−1 and around 1460 cm−1.

20. The method of claim 1, wherein the contaminant includes BRAYCOTE® 248.

21. The method of claim 1, wherein the at least two wavenumbers are around 2924 cm−1 and around 752 cm−1.

22. The method of claim 1, wherein the at least two wavenumbers are around 925 cm−1 and around 2190 cm−1.

23. The method of claim 1, wherein the contaminant includes ALODINE® 1200.

24. The method of claim 1, wherein the at least two wavenumbers are around 1060 cm−1 and around 1600 cm−1.

25. The method of claim 1, wherein the contaminant includes ALKASOL 27.

26. The method of claim 1, wherein the at least two wavenumbers are around 1241 cm−1 and around 2551 cm−1.

27. The method of claim 1, wherein the contaminant includes JET CLEAN E.

28. The method of claim 1, wherein the at least two wavenumbers are around 1120 cm−1 and around 901 cm−1.

29. The method of claim 1, wherein the contaminant includes PACE B82.

30. The method of claim 1, wherein the at least two wavenumbers are around 1180 cm−1 and around 1620 cm−1.

31. The method of claim 1, wherein the contaminant includes SNOOP.

32. The method of claim 1, wherein the at least two wavenumbers are around 1170 cm−1 and around 3300 cm−1.

33. The method of claim 1, wherein the contaminant includes SPRAYLAT.

34. The method of claim 1, wherein the at least two wavenumbers are around 1730 cm−1 and around 1160 cm−1.

35. The method of claim 1, wherein the contaminant includes AZTEC.

36. The method of claim 1, wherein the at least two wavenumbers are around 1259 cm−1 and around 800 cm−1.

37. The method of claim 1, wherein the contaminant includes silicone.

38. The method of claim 1, wherein the at least two wavenumbers are around 1212 cm−1 and around 1155 cm−1.

39. The method of claim 1, wherein the contaminant includes TEFLON®.

40. The method of claim 1, wherein the at least two wavenumbers are around 1745 cm−1 and around 1180 cm−1.

41. The method of claim 1, wherein the contaminant includes lanolin.

42. The method of claim 1, wherein the at least two wavenumbers are around 2924 cm−1 and around 1751 cm−1.

43. The method of claim 1, wherein the contaminant includes fingerprints.

44. The method of claim 1, wherein the at least two wavenumbers are around 3425 cm−1 and around 3195 cm−1.

45. The method of claim 1, wherein the contaminant includes urea.

46. The method of claim 1, wherein the at least two wavenumbers are around 1650 cm−1 and around 3300 cm−1.

47. The method of claim 1, wherein the contaminant includes collagen.

48. The method of claim 1, wherein the at least two wavenumbers are around 1681 cm−1 and around 1230 cm−1.

49. The method of claim 1, wherein the contaminant includes polyurethane paint.

50. The method of claim 1, wherein the at least two wavenumbers are around 1502 cm−1 and around 2924 cm−1.

51. The method of claim 1, wherein the contaminant includes epoxy primer.

52. The method of claim 1, wherein the at least two wavenumbers are around 1709 cm−1 and around 960 cm−1.

53. The method of claim 1, wherein the contaminant includes methyl ethyl ketone.

54. A non-destructive method for identifying a contaminant on a sample, the method comprising:
transmitting an infrared beam onto a sample;
detecting a reflected infrared beam reflected by the sample;
determining a first infrared absorbance peak of the sample from the reflected infrared beam at a first wavenumber;
determining a second infrared absorbance peak of the sample from the reflected infrared beam at a second wavenumber; and
identifying the contaminant by correlating the first infrared absorbance peak and the second infrared absorbance peak to a reference sample.

55. The method of claim 54, wherein the reference sample shows the first infrared absorbance peak at the first wavenumber and the second absorbance peak at the second wavenumber.

56. The method of claim 54, wherein determining at least one of the first infrared absorbance and the second infrared absorbance includes utilizing an infrared spectrometer.

57. The method of claim 56, wherein the infrared spectrometer includes an infrared filter spectrometer.

58. The method of claim 56, wherein the infrared spectrometer includes an ellipsoidal mirror collector.

59. The method of claim 56, wherein the infrared spectrometer includes an attenuated total reflectance collector.

60. The method of claim 56, wherein the infrared spectrometer includes at least two filters.

61. The method of claim 60, wherein the at least two filters include narrow bandpass infrared filters.

62. The method of claim 54, wherein the first wave number is around 2924 cm−1 and the second wavenumber is around 1739 cm−1.

63. The method of claim 54, wherein the first wave number is around 2933 cm−1 and the second wavenumber is around 1739 cm−1.

64. The method of claim 54, wherein the contaminant includes grease.

65. The method of claim 54, wherein the first wave number is around 1071 cm−1 and the second wavenumber is around 3279 cm−1.

66. The method of claim 54, wherein the contaminant includes BOELUBE®.

67. The method of claim 54, wherein the first wave number is around 1745 cm−1 and the second wavenumber is around 1170 cm−1.

68. The method of claim 54, wherein the contaminant includes MICROCUT®.

69. The method of claim 54, wherein the first wave number is around 2924 cm−1 and the second wavenumber is around 1060 cm−1.

70. The method of claim 54, wherein the contaminant includes DINITROL® AV8.

71. The method of claim 54, wherein the first wave number is around 2924 cm−1 and the second wavenumber is around 752 cm−1.

72. The method of claim 54, wherein the contaminant includes DINITROL® AV30.

73. The method of claim 54, wherein the first wave number is around 2924 cm−1 and the second wavenumber is around 1460 cm−1.

74. The method of claim 54, wherein the contaminant includes BRAYCOTE® 248.

75. The method of claim 54, wherein the first wave number is around 2924 cm−1 and the second wavenumber is around 752 cm−1.

76. The method of claim 54, wherein the first wave number is around 925 cm−1 and the second wavenumber is around 2190 cm−1.

77. The method of claim 54, wherein the contaminant includes ALODINIE® 1200.

78. The method of claim 54, wherein the first wave number is around 1060 cm−1 and the second wavenumber is around 1600 cm−1.

79. The method of claim 54, wherein the contaminant includes ALKASOL 27.

80. The method of claim 54, wherein the first wave number is around 1241 cm−1 and the second wavenumber is around 2551 cm−1.

81. The method of claim 54, wherein the contaminant includes JET CLEAN E.

82. The method of claim 54, wherein the first wave number is around 1120 cm−1 and the second wavenumber is around 901 cm−1.

83. The method of claim 54, wherein the contaminant includes PACE B82.

84. The method of claim 54, wherein the first wave number is around 1180 cm−1 and the second wavenumber is around 1620 cm−1.

85. The method of claim 54, wherein the contaminant includes SNOOP.

86. The method of claim 54, wherein the first wave number is around 1170 cm−1 and the second wavenumber is around 3300 cm−1.

87. The method of claim 54, wherein the contaminant includes SPRAYLAT.

88. The method of claim 54, wherein the first wave number is around 1730 cm−1 and the second wavenumber is around 1160 cm−1.

89. The method of claim 54, wherein the contaminant includes AZTEC.

90. The method of claim 54, wherein the first wave number is around 1259 cm−1 and the second wavenumber is around 800 cm−1.

91. The method of claim 54, wherein the contaminant includes silicone.

92. The method of claim 54, wherein the first wave number is around 1212 cm−1 and the second wavenumber is around 1155 cm−1.

93. The method of claim 54, wherein the contaminant includes TEFLON®.

94. The method of claim 54, wherein the first wave number is around 1745 cm−1 and the second wavenumber is around 1180 cm−1.

95. The method of claim 54, wherein the contaminant includes lanolin.

96. The method of claim 54, wherein the first wave number is around 2924 cm−1 and the second wavenumber is around 1751 cm−1.

97. The method of claim 54, wherein the contaminant includes fingerprints.

98. The method of claim 54, wherein the first wave number is around 3425 cm−1 and the second wavenumber is around 3195 cm−1.

99. The method of claim 54, wherein the contaminant includes urea.

100. The method of claim 54, wherein the first wave number is around 1650 cm−1 and the second wavenumber is around 3300 cm−1.

101. The method of claim 54, wherein the contaminant includes collagen.

102. The method of claim 54, wherein the first wave number is around 1681 cm−1 and the second wavenumber is around 1230 cm−1.

103. The method of claim 54, wherein the contaminant includes polyurethane paint.

104. The method of claim 54, wherein the first wave number is around 1502 cm−1 and the second wavenumber is around 2924 cm−1.

105. The method of claim 54, wherein the contaminant includes epoxy primer.

106. The method of claim 54, wherein the first wave number is around 1709 cm−1 and the second wavenumber is around 960 cm−1.

107. The method of claim 54, wherein the contaminant includes methyl ethyl ketone.

108. A non-destructive method for detecting a contaminant on a sample, the method comprising:
   transmitting an infrared beam onto a sample;
   detecting a reflected infrared beam reflected by the sample;
   determining a first infrared absorbance peak of the sample from the reflected infrared beam at a first wavenumber;
   correlating the first infrared absorbance peak to a first absorbance peak of a contaminant at the first wavenumber;
   determining a second infrared absorbance peak of the sample from the reflected infrared beam at a second wavenumber; and
   confirming a presence of a predetermined amount of the contaminant on the surface by correlating the second infrared absorbance peak to a second absorbance peak of the contaminant at the second wavenumber.

109. The method of claim 108, wherein determining at least one of the first infrared absorbance and the second infrared absorbance includes utilizing an infrared spectrometer.

110. The method of claim 109, wherein the infrared spectrometer includes an infrared filter spectrometer.

111. The method of claim 109, wherein the infrared spectrometer includes an ellipsoidal mirror collector.

112. The method of claim 109, wherein the infrared spectrometer includes an attenuated total reflectance collector.

113. The method of claim 109, wherein the infrared spectrometer includes at least two filters.

114. The method of claim 113, wherein the at least two filters include narrow bandpass infrared filters.

115. The method of claim 108, wherein the first wave number is around 2924 cm−1 and the second wavenumber is around 1739 cm−1.

116. The method of claim 108, wherein the first wave number is around 2933 cm−1 and the second wavenumber is around 1739 cm−1.

117. The method of claim 108, wherein the contaminant includes grease.

118. The method of claim 108, wherein the first wave number is around 1071 cm−1 and the second wavenumber is around 3279 cm−1.

119. The method of claim 108, wherein the contaminant includes BOELUBE®.

120. The method of claim 108, wherein the first wave number is around 1745 cm−1 and the second wavenumber is around 1170 cm−1.

121. The method of claim 108, wherein the contaminant includes MICROCUT®.

122. The method of claim 108, wherein the first wave number is around 2924 cm−1 and the second wavenumber is around 1060 cm−1.

123. The method of claim 108, wherein the contaminant includes DINITROL® AV8.

124. The method of claim 108, wherein the first wave number is around 2924 cm−1 and the second wavenumber is around 752 cm−1.

125. The method of claim 108, wherein the contaminant includes DINITROL® AV30.

126. The method of claim 108, wherein the first wave number is around 2924 cm−1 and the second wavenumber is around 1460 cm−1.

127. The method of claim 108, wherein the contaminant includes BRAYCOTE® 248.

128. The method of claim 108, wherein the first wave number is around 2924 cm−1 and the second wavenumber is around 752 cm−1.

129. The method of claim 108, wherein the first wave number is around 925 cm−1 and the second wavenumber is around 2190 cm−1.

130. The method of claim 108, wherein the contaminant includes ALODINE® 1200.

131. The method of claim 108, wherein the first wave number is around 1060 cm−1 and the second wavenumber is around 1600 cm−1.

132. The method of claim 108, wherein the contaminant includes ALKASOL 27.

133. The method of claim 108, wherein the first wave number is around 1241 cm−1 and the second wavenumber is around 2551 cm−1.

134. The method of claim 108, wherein the contaminant includes JET CLEAN E.

135. The method of claim 108, wherein the first wave number is around 1120 cm−1 and the second wavenumber is around 901 cm−1.

136. The method of claim 108, wherein the contaminant includes PACE B82.

137. The method of claim 108, wherein the first wave number is around 1180 cm−1 and the second wavenumber is around 1620 cm−1.

138. The method of claim 108, wherein the contaminant includes SNOOP.

139. The method of claim 108, wherein the first wave number is around 1170 cm−1 and the second wavenumber is around 3300 cm−1.

140. The method of claim 108, wherein the contaminant includes SPRAYLAT.

141. The method of claim 108, wherein the first wave number is around 1730 cm−1 and the second wavenumber is around 1160 cm−1.

142. The method of claim 108, wherein the contaminant includes AZTEC.

143. The method of claim 108, wherein the first wave number is around 1259 cm−1 and the second wavenumber is around 800 cm−1.

144. The method of claim 108, wherein the contaminant includes silicone.

145. The method of claim 108, wherein the first wave number is around 1212 cm−1 and the second wavenumber is around 1155 cm−1.

146. The method of claim 108, wherein the contaminant includes TEFLON®.

147. The method of claim 108, wherein the first wave number is around 1745 cm−1 and the second wavenumber is around 1180 cm−1.

148. The method of claim 108, wherein the contaminant includes lanolin.

149. The method of claim 108, wherein the first wave number is around 2924 cm−1 and the second wavenumber is around 1751 cm−1.

150. The method of claim 108, wherein the contaminant includes fingerprints.

151. The method of claim 108, wherein the first wave number is around 3425 cm−1 and the second wavenumber is around 3195 cm−1.

152. The method of claim 108, wherein the contaminant includes urea.

153. The method of claim 108, wherein the first wave number is around 1650 cm−1 and the second wavenumber is around 3300 cm−1.

154. The method of claim 108, wherein the contaminant includes collagen.

155. The method of claim 108, wherein the first wave number is around 1681 cm−1 and the second wavenumber is around 1230 cm−1.

156. The method of claim 108, wherein the contaminant includes polyurethane paint.

157. The method of claim 108, wherein the first wave number is around 1502 cm−1 and the second wavenumber is around 2924 cm−1.

158. The method of claim 108, wherein the contaminant includes epoxy primer.

159. The method of claim 108, wherein the first wave number is around 1709 cm−1 and the second wavenumber is around 960 cm−1.

160. The method of claim 108, wherein the contaminant includes methyl ethyl ketone.

* * * * *